US009423436B2

(12) United States Patent
Bellin et al.

(10) Patent No.: US 9,423,436 B2
(45) Date of Patent: Aug. 23, 2016

(54) METHOD AND APPARATUS TO ASSESS THE THERMAL DAMAGE CAUSED TO A PCD CUTTER USING CAPACITANCE SPECTROSCOPY

(71) Applicant: Varel International Ind., L.P., Carrollton, TX (US)

(72) Inventors: Federico Bellin, Tomball, TX (US); Vamsee Chintamaneni, Houston, TX (US)

(73) Assignee: VAREL INTERNATIONAL IND., L.P., Carrollton, TX (US)

( * ) Notice: Subject to any disclaimer, the term of this patent is extended or adjusted under 35 U.S.C. 154(b) by 265 days.

(21) Appl. No.: 14/073,557

(22) Filed: Nov. 6, 2013

(65) Prior Publication Data

US 2014/0062509 A1    Mar. 6, 2014

Related U.S. Application Data

(63) Continuation-in-part of application No. 13/401,188, filed on Feb. 21, 2012.

(51) Int. Cl.
| | | |
|---|---|---|
| *G01N 27/22* | (2006.01) | |
| *G01R 27/26* | (2006.01) | |
| *G01N 33/40* | (2006.01) | |

(52) U.S. Cl.
CPC .......... *G01R 27/2605* (2013.01); *G01N 27/22* (2013.01); *G01N 33/40* (2013.01)

(58) Field of Classification Search
CPC .................................................. G01N 27/22
See application file for complete search history.

(56) References Cited

U.S. PATENT DOCUMENTS

| | | | |
|---|---|---|---|
| 2,755,240 | A | 7/1956 | Normore et al. |
| 2,934,811 | A | 5/1960 | Wellington |
| 4,255,976 | A | 3/1981 | Formato |

(Continued)

FOREIGN PATENT DOCUMENTS

| | | |
|---|---|---|
| DE | 102005040296 | 2/2007 |
| EP | 2631638 | 8/2013 |
| WO | 2013003333 | 1/2013 |

OTHER PUBLICATIONS

Copenheaver, Blaine R, International Search Report and Written Opinion of the International Searching Authority for PCT/US2013/026938, Apr. 25, 2013, pp. 1-13.

(Continued)

*Primary Examiner* — Tung X Nguyen
*Assistant Examiner* — Feba Pothen

(57) ABSTRACT

A method and apparatus for non-destructively determining the wear resistance of an ultra-hard polycrystalline structure after being coupled to a downhole tool using capacitance measurements. The apparatus includes a capacitance measuring device having a positive and negative terminal, a leached component comprising a polycrystalline structure that has been coupled to a downhole tool, a first wire, and a second wire. The first wire electrically couples the positive terminal to a surface of the leached component and the second wire electrically couples the negative terminal to a surface of the downhole tool. The capacitance is measured for the leached component one or more times and compared to a calibration curve that shows a relationship between capacitance values and wear resistance, thereby allowing determination of an estimated wear resistance for the polycrystalline structure.

18 Claims, 10 Drawing Sheets

(56) References Cited

U.S. PATENT DOCUMENTS

| | | | |
|---|---|---|---|
| 4,290,016 | A | 9/1981 | Lorenzi |
| 4,952,869 | A | 8/1990 | Tuttle |
| 6,063,333 | A | 5/2000 | Dennis |
| 6,107,808 | A | 8/2000 | McKee et al. |
| 6,388,453 | B1 | 5/2002 | Greer |
| 6,437,579 | B1 | 8/2002 | Yamashita et al. |
| 7,558,369 | B1 | 7/2009 | Mourik et al. |
| 7,616,734 | B1 | 11/2009 | Corbett et al. |
| 7,712,553 | B2 | 5/2010 | Shamburger |
| 7,757,792 | B2 | 7/2010 | Shamburger |
| 8,014,492 | B1 | 9/2011 | Corbett et al. |
| 8,080,074 | B2 | 12/2011 | Sani |
| 2002/0053904 | A1 | 5/2002 | Chen et al. |
| 2002/0179864 | A1 | 12/2002 | Fielden |
| 2005/0016649 | A1* | 1/2005 | Poulbot ............. B60C 11/24 152/154.2 |
| 2005/0050801 | A1 | 3/2005 | Cho et al. |
| 2006/0192568 | A1 | 8/2006 | Pasero et al. |
| 2006/0244443 | A1 | 11/2006 | Goldfine et al. |
| 2007/0079994 | A1 | 4/2007 | Middlemiss |
| 2007/0131458 | A1 | 6/2007 | Shen et al. |
| 2007/0169419 | A1 | 7/2007 | Davis et al. |
| 2008/0054891 | A1 | 3/2008 | Dobsky |
| 2008/0104034 | A1 | 5/2008 | Stewart et al. |
| 2008/0121433 | A1 | 5/2008 | Ledgerwood |
| 2008/0164887 | A1 | 7/2008 | Schroder |
| 2008/0185189 | A1 | 8/2008 | Griffo et al. |
| 2008/0223623 | A1 | 9/2008 | Keshavan et al. |
| 2008/0241024 | A1* | 10/2008 | Riekkola-Vanhanen C22B 15/0008 423/27 |
| 2008/0290866 | A1 | 11/2008 | Cuffe et al. |
| 2009/0152018 | A1 | 6/2009 | Sani |
| 2009/0173015 | A1 | 7/2009 | Keshavan et al. |
| 2010/0011673 | A1 | 1/2010 | Shamburger |
| 2010/0095602 | A1 | 4/2010 | Belnap et al. |
| 2010/0155149 | A1 | 6/2010 | Keshavan et al. |
| 2010/0231208 | A1 | 9/2010 | Huggett et al. |
| 2010/0314176 | A1* | 12/2010 | Zhang ............... E21B 10/573 175/383 |
| 2011/0024201 | A1* | 2/2011 | Scott ................ B22F 7/004 175/428 |
| 2011/0120782 | A1 | 5/2011 | Cooley et al. |
| 2011/0215814 | A1 | 9/2011 | Dorrough |
| 2011/0258936 | A1 | 10/2011 | DiGiovanni |
| 2012/0047815 | A1 | 3/2012 | Sani |
| 2012/0055717 | A1 | 3/2012 | Liversage et al. |
| 2012/0067652 | A1 | 3/2012 | Bellin |
| 2012/0211284 | A1 | 8/2012 | DiGiovanni |
| 2012/0241224 | A1 | 9/2012 | Qian et al. |
| 2013/0001100 | A1 | 1/2013 | Thigpen et al. |
| 2013/0213433 | A1 | 8/2013 | Bellin et al. |
| 2013/0213720 | A1 | 8/2013 | Bellin et al. |
| 2013/0214768 | A1 | 8/2013 | Chintamaneni et al. |
| 2013/0214769 | A1 | 8/2013 | King et al. |
| 2013/0214799 | A1 | 8/2013 | Bellin et al. |
| 2013/0247478 | A1 | 9/2013 | Bellin et al. |
| 2013/0248258 | A1 | 9/2013 | Bellin et al. |
| 2014/0062509 | A1 | 3/2014 | Bellin et al. |
| 2014/0253149 | A1 | 9/2014 | Bellin |

OTHER PUBLICATIONS

Copenheaver, Blaine R, International Search Report and Written Opinion of the International Searching Authority for PCT/US2013/026918, Apr. 23, 2013, pp. 1-11.

Copenheaver, Blaine R, International Search Report and Written Opinion of the International Searching Authority for PCT/US2013/026931, Apr. 26, 2013, pp. 1-10.

Bellin et al., "The Current State of PDC Bit Technology Part 2 of 3: Leaching a Thin Layer at the Working Surface of a PDC Cutter to Remove the Cobalt Dramatically Reduces Diamond Degradation Due to Frictional Heat", Oct. 1, 2010, pp. 1-18, Retrieved from the Internet: URL: http://www.varelintl.com/content/includes/world_oil_october 2010.pdf [retrieved on Mar. 18, 2014].

Bellin et al., "The Current State of PDC Bit Technology Part 2 of 3: Improvements in Material Properties and Testing Methods Are Being Pursued to Make PDC the Cutter of Choice for an Increasing Variety of Applications" Nov. 1, 2010, pp. 67-71, Retrieved from the Internet: URL: http://www.vareintl.com/content/includes/pdc_technology_part_3.pdf.

Pierson, Hugh O., Chapter 12: Natural High-Pressure Synthetic Diamond, Handbook of Carbon, Graphite, Diamond and Fullerences, Properties, Processing and Applications, Jan. 1, 1993, pp. 278-301, Noyes Publications.

Kraus, Leonie, European Search Report EP Application No. 13156142, Mar. 19, 2014, 7 pages, place of search The Hague.

Kraus, Leonie, European Search Report EP Application No. 13156143, Feb. 19, 2014, 6 pages, place of search The Hague.

Translation of Description of WO/2007022749 corresponding to International Application No. PCT/DE2006/001376 "Measuring Method for In-Situ Control of the Chemical Etching Process of Latent Ion Tracks in a Dielectric Substrate" printed on Nov. 14, 2004, 4 pages, http://patentscope.wipo.int/search/en/detail/jsf, unofficial translation via Google translate.

Gill Jennings & Avery LLP, Henry Hunt-Grubbe, Response to extended European Search Report (EESR) issued in European Patent Application No. 13156142.5, dated Oct. 30, 2014, 25 pages.

Thomas, Shane, International Search Report and Written Opinion issued in PCT/US2014/064359, completed on Jan. 18, 2015, 11 pages, United States Patent and Trademark Office, Alexandria, Virginia, United States.

Forestier, Gilles, European Search Report issued in European Patent Application No. 13156140.9,completed on Jan. 12, 2015, 8 pages, European Patent Office, The Hague.

Forestier, Gilles, European Search Report issued in European Patent Application No. 13156138.3, completed on Jan. 12, 2015, 8 pages, European Patent Office, The Hague.

Copenheaver, Blain, International Search Report and Written Opinion issued in international application No. PCT/US2015/028308, completed Jul. 2, 2015, mailed Jul. 29, 2015, 10 pages, United States Patent and Trademark Office, Alexandria, Virginia, United States.

Fluke Multimeters, 1995.

Kraus, Leonie, European Search Report issued in European Application No. 15166121, completion date Sep. 21, 2015, mailing date Sep. 29, 2015, 7 pages, European Patent Office, The Hague.

Grove et al., Determining Dielectric Constants Using a Parallel Plate Capacitor, American Journal of Physics 73 (1), Jan. 2005, entire document. [retrieved on Apr. 4, 2013]. Retrieved form Internet <URL: http://users.df.uba.ar/sgil/physics_paper_doc/papers_phys/e&m/dielectr_const_2k4.pdf>entire document.

* cited by examiner

METHOD AND APPARATUS TO ASSESS THE THERMAL DAMAGE CAUSED TO A PCD CUTTER USING CAPACITANCE SPECTROSCOPY

CROSS-REFERENCES TO RELATED APPLICATIONS

This application is a continuation-in-part application of and claims priority under 35 U.S.C. §120 to U.S. patent application Ser. No. 13/401,188, titled "Use Of Capacitance To Analyze Polycrystalline Diamond," filed Feb. 21, 2012. The complete disclosure of the foregoing priority application is hereby fully incorporated by reference herein.

The present application is related to U.S. patent application Ser. No. 13/401,335, entitled "Use of Capacitance and Eddy Currents to Analyze Polycrystalline Diamond" and filed on Feb. 21, 2012, and U.S. patent application Ser. No. 13/401,452, entitled "Method To Improve The Performance Of A Leached Cutter" and filed on Feb. 21, 2012, which are all incorporated by reference herein.

TECHNICAL FIELD

The present invention relates generally to a method and apparatus for measuring characteristics of one or more regions within an ultra-hard polycrystalline structure; and more particularly, to a non-destructive method and apparatus for determining any thermal damage taken by a ultra-hard polycrystalline structure, such as the ones used in forming polycrystalline diamond compact ("PDC") cutters, that has been leached to a desired depth upon being exposed to high temperatures, such as the brazing process for coupling the PDC cutter to a drill bit or the like.

BACKGROUND

Polycrystalline diamond compacts ("PDC") have been used in industrial applications, including rock drilling applications and metal machining applications. Such compacts have demonstrated advantages over some other types of cutting elements, such as better wear resistance and impact resistance. The PDC can be formed by sintering individual diamond particles together under the high pressure and high temperature ("HPHT") conditions referred to as the "diamond stable region," which is typically above forty kilobars and between 1,200 degrees Celsius and 2,000 degrees Celsius, in the presence of a catalyst/solvent which promotes diamond-diamond bonding. Some examples of catalyst/solvents for sintered diamond compacts are cobalt, nickel, iron, and other Group VIII metals. PDCs usually have a diamond content greater than seventy percent by volume, with about eighty percent to about ninety-eight percent being typical. An unbacked PDC can be mechanically bonded to a tool (not shown), according to one example. Alternatively, the PDC is bonded to a substrate, thereby forming a PDC cutter, which is typically insertable within a downhole tool (not shown), such as a drill bit or a reamer.

FIG. 1 shows a side view of a PDC cutter 100 having a polycrystalline diamond ("PCD") cutting table 110, or compact, in accordance with the prior art. Although a PCD cutting table 110 is described in the exemplary embodiment, other types of cutting tables, including polycrystalline boron nitride ("PCBN") compacts, are used in alternative types of cutters. Referring to FIG. 1, the PDC cutter 100 typically includes the PCD cutting table 110 and a substrate 150 that is coupled to the PCD cutting table 110. The PCD cutting table 110 is about one hundred thousandths of an inch (2.5 millimeters) thick; however, the thickness is variable depending upon the application in which the PCD cutting table 110 is to be used.

The substrate 150 includes a top surface 152, a bottom surface 154, and a substrate outer wall 156 that extends from the circumference of the top surface 152 to the circumference of the bottom surface 154. The PCD cutting table 110 includes a cutting surface 112, an opposing surface 114, and a PCD cutting table outer wall 116 that extends from the circumference of the cutting surface 112 to the circumference of the opposing surface 114. The opposing surface 114 of the PCD cutting table 110 is coupled to the top surface 152 of the substrate 150. Typically, the PCD cutting table 110 is coupled to the substrate 150 using a high pressure and high temperature ("HPHT") press. However, other methods known to people having ordinary skill in the art can be used to couple the PCD cutting table 110 to the substrate 150. In one embodiment, upon coupling the PCD cutting table 110 to the substrate 150, the cutting surface 112 of the PCD cutting table 110 is substantially parallel to the substrate's bottom surface 154. Additionally, the PDC cutter 100 has been illustrated as having a right circular cylindrical shape; however, the PDC cutter 100 is shaped into other geometric or non-geometric shapes in other exemplary embodiments. In certain exemplary embodiments, the opposing surface 114 and the top surface 152 are substantially planar; however, the opposing surface 114 and the top surface 152 are non-planar in other exemplary embodiments. Additionally, according to some exemplary embodiments, a bevel (not shown) is formed around at least the circumference of the cutting surface 112.

According to one example, the PDC cutter 100 is formed by independently forming the PCD cutting table 110 and the substrate 150, and thereafter bonding the PCD cutting table 110 to the substrate 150. Alternatively, the substrate 150 is initially formed and the PCD cutting table 110 is subsequently formed on the top surface 152 of the substrate 150 by placing polycrystalline diamond powder onto the top surface 152 and subjecting the polycrystalline diamond powder and the substrate 150 to a high temperature and high pressure process. Alternatively, the substrate 150 and the PCD cutting table 110 are formed and bonded together at about the same time. Although a few methods of forming the PDC cutter 100 have been briefly mentioned, other methods known to people having ordinary skill in the art can be used.

According to one example for forming the PDC cutter 100, the PCD cutting table 110 is formed and bonded to the substrate 150 by subjecting a layer of diamond powder and a mixture of tungsten carbide and cobalt powders to HPHT conditions. The cobalt is typically mixed with tungsten carbide and positioned where the substrate 150 is to be formed. The diamond powder is placed on top of the cobalt and tungsten carbide mixture and positioned where the PCD cutting table 110 is to be formed. The entire powder mixture is then subjected to HPHT conditions so that the cobalt melts and facilitates the cementing, or binding, of the tungsten carbide to form the substrate 150. The melted cobalt also diffuses, or infiltrates, into the diamond powder and acts as a catalyst for synthesizing diamond bonds and forming the PCD cutting table 110. Thus, the cobalt acts as both a binder for cementing the tungsten carbide and as a catalyst/solvent for sintering the diamond powder to form diamond-diamond bonds. The cobalt also facilitates in forming strong bonds between the PCD cutting table 110 and the cemented tungsten carbide substrate 150.

Cobalt has been a preferred constituent of the PDC manufacturing process. Traditional PDC manufacturing processes use cobalt as the binder material for forming the substrate 150 and also as the catalyst material for diamond synthesis because of the large body of knowledge related to using cobalt in these processes. The synergy between the large bodies of knowledge and the needs of the process have led to using cobalt as both the binder material and the catalyst material. However, as is known in the art, alternative metals, such as iron, nickel, chromium, manganese, and tantalum, and other suitable materials, can be used as a catalyst for diamond synthesis. When using these alternative materials as a catalyst for diamond synthesis to form the PCD cutting table 110, cobalt, or some other material such as nickel chrome or iron, is typically used as the binder material for cementing the tungsten carbide to form the substrate 150. Although some materials, such as tungsten carbide and cobalt, have been provided as examples, other materials known to people having ordinary skill in the art can be used to form the substrate 150, the PCD cutting table 110, and the bonds between the substrate 150 and the PCD cutting table 110.

FIG. 2 is a schematic microstructural view of the PCD cutting table 110 of FIG. 1 in accordance with the prior art. Referring to FIGS. 1 and 2, the PCD cutting table 110 has diamond particles 210 bonded to other diamond particles 210, one or more interstitial spaces 212 formed between the diamond particles 210, and cobalt 214, or some other catalyst, deposited within one or more of the interstitial spaces 212. During the sintering process, the interstitial spaces 212, or voids, are formed between the carbon-carbon bonds and are located between the diamond particles 210. The diffusion of cobalt 214 into the diamond powder results in cobalt 214 being deposited within these interstitial spaces 212 that are formed within the PCD cutting table 110 during the sintering process.

Once the PCD cutting table 110 is formed and placed into operation, the PCD cutting table 110 is known to wear quickly when the temperature reaches a critical temperature. This critical temperature is about 750 degrees Celsius and is reached when the PCD cutting table 110 is cutting rock formations or other known materials. The high rate of wear is believed to be caused by the differences in the thermal expansion rate between the diamond particles 210 and the cobalt 214 and also by the chemical reaction, or graphitization, that occurs between cobalt 214 and the diamond particles 210. The coefficient of thermal expansion for the diamond particles 210 is about $1.0 \times 10^{-6}$ millimeters$^{-1} \times$ Kelvin$^{-1}$ ("mm$^{-1}$K$^{-1}$"), while the coefficient of thermal expansion for the cobalt 214 is about $13.0 \times 10^{-6}$ mm$^{-1}$K$^{-1}$. Thus, the cobalt 214 expands much faster than the diamond particles 210 at temperatures above this critical temperature, thereby making the bonds between the diamond particles 210 unstable. The PCD cutting table 110 becomes thermally degraded at temperatures above about 750 degrees Celsius and its cutting efficiency deteriorates significantly.

Efforts have been made to slow the wear of the PCD cutting table 110 at these high temperatures. These efforts include performing a leaching process on the PCD cutting table 110, which removes some of the cobalt 214 from the interstitial spaces 212. These leaching processes, which includes, but is not limited to, an acid leaching process and/or an electrolytic leaching process, is known to persons having ordinary skill in the art and is not described herein for the sake of brevity. By removing some of the cobalt 214, or catalyst, from the PCD cutting table 110, the thermal degradation of the PCD structure is reduced.

FIG. 3 shows a cross-section view of a leached PDC cutter 300 having a PCD cutting table 310 that has been at least partially leached in accordance with the prior art. Referring to FIG. 3, the PDC cutter 300 includes the PCD cutting table 310 coupled to a substrate 350. The substrate 350 is similar to substrate 150 (FIG. 1) and is not described again for the sake of brevity. The PCD cutting table 310 is similar to the PCD cutting table 110 (FIG. 1), but includes a leached layer 354 and an unleached layer 356. The leached layer 354 extends from the cutting surface 312, which is similar to the cutting surface 112 (FIG. 1), towards an opposing surface 314, which is similar to the opposing surface 114 (FIG. 1). In the leached layer 354, at least a portion of the cobalt 214 has been removed from within the interstitial spaces 212 (FIG. 2) using at least one leaching process mentioned above. Thus, the leached layer 354 has been leached to a desired depth 353. However, during the leaching process, one or more by-product materials 398 are formed and deposited within some of the interstitial spaces 212 (FIG. 2) in the leached layer 354. These by-product materials 398 may be removed from the leached layer 354 in certain applications by methods known to people having ordinary skill in the art. The unleached layer 356 is similar to the PCD cutting table 150 (FIG. 1) and extends from the end of the leached layer 354 to the opposing surface 314. In the unleached layer 356, the cobalt 214 (FIG. 2) remains within the interstitial spaces 212 (FIG. 2). Although a boundary line 355 is formed between the leached layer 354 and the unleached layer 356 and is depicted as being substantially linear, the boundary line 355 can be non-linear.

The leached PDC cutters 300 are leached to different desired depths 353 and how deep the cutter 300 has been leached has an effect on the performance of the cutter 300. Conventionally, the leached depth 353 of the cutter 300 is measured, or determined, by cutting the cutter 300 vertically in half and then subsequently polishing the cutter 300. The leached depth 353 is visually measured under a microscope or similar magnifying device. This process is rather tedious and cumbersome as it involves cutting the cutter 300, such as by electrical discharge machining ("EDM"), mounting, grinding, and polishing the cutter 300, and performing an analysis under a microscope. Additionally, this process destroys the cutter 300 from subsequently being used. The leached depth 353 that is determined in this manner is assumed to be the same leached depth in other cutters that were leached in the same batch.

The leached PDC cutters 300 are typically brazed onto a drill bit head, or other downhole tool, by means of a blow torch. During this brazing process, the leached PDC cutters 300 can be damaged by the prolonged exposure to too high temperatures. The exposure to high heat for a prolonged time period can cause the catalyst to move around within the diamond table, thereby changing the leaching depth and affecting the performance of the cutters 300. These damaged leached PDC cutters 300 will cause the bit to underperform in the field. At the moment, there is no current technology available to the bit manufacturer that allows quantifying, or objectively determining, the amount of thermal damage taken by the leached PDC cutter 300 during the brazing process in a non-destructive manner.

BRIEF DESCRIPTION OF THE DRAWINGS

The foregoing and other features and aspects of the invention are best understood with reference to the following description of certain exemplary embodiments, when read in conjunction with the accompanying drawings, wherein.

Figure 1:
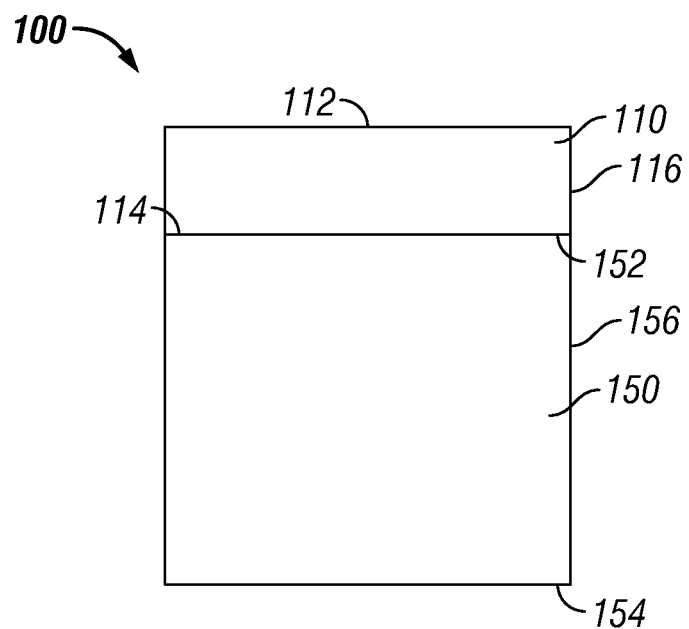
FIG. 1 is a side view of a PDC cutter having a polycrystalline diamond cutting table, or compact, in accordance with the prior art.
Figure 2:
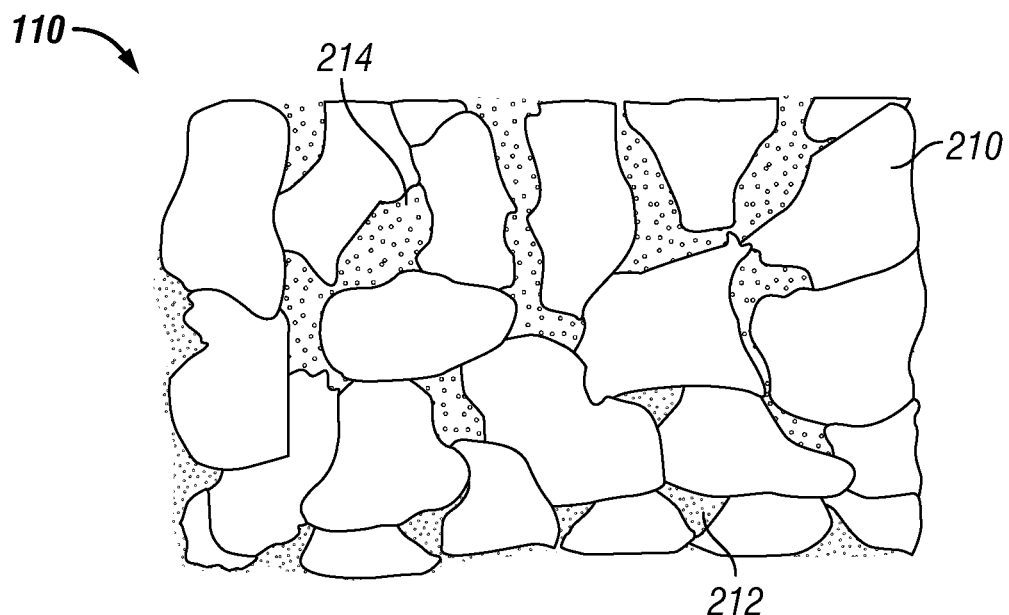
FIG. 2 is a schematic microstructural view of the PCD cutting table of FIG. 1 in accordance with the prior art.

The drawings illustrate only exemplary embodiments of the invention and are therefore not to be considered limiting of its scope, as the invention may admit to other equally effective embodiments.

BRIEF DESCRIPTION OF EXEMPLARY EMBODIMENTS

The present invention is directed to a non-destructive method and apparatus for determining any thermal damage taken by a ultra-hard polycrystalline structure, such as the ones used in forming polycrystalline diamond compact ("PDC") cutters, that has been leached to a desired depth upon being exposed to high temperatures, such as the brazing process for coupling the PDC cutter to a drill bit or the like. Although the description of exemplary embodiments is provided below in conjunction with a PDC cutter, alternate embodiments of the invention may be applicable to other types of polycrystalline structures including, but not limited to, PCBN cutters. Further, according to some exemplary embodiments, one or more portions of the methods described below is implemented using an electronic measuring device. For example, the capacitance is measured using a capacitance measuring device. The invention is better understood by reading the following description of non-limiting, exemplary embodiments with reference to the attached drawings, wherein like parts of each of the figures are identified by like reference characters, and which are briefly described as follows.

Figure 3:
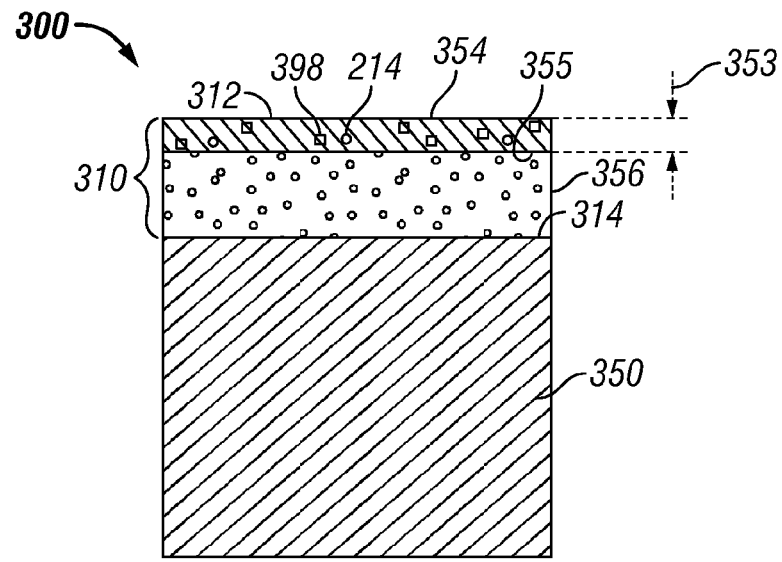
FIG. 3 is a cross-section view of a PDC cutter having a PCD cutting table that has been at least partially leached in accordance with the prior art.
Figure 4:
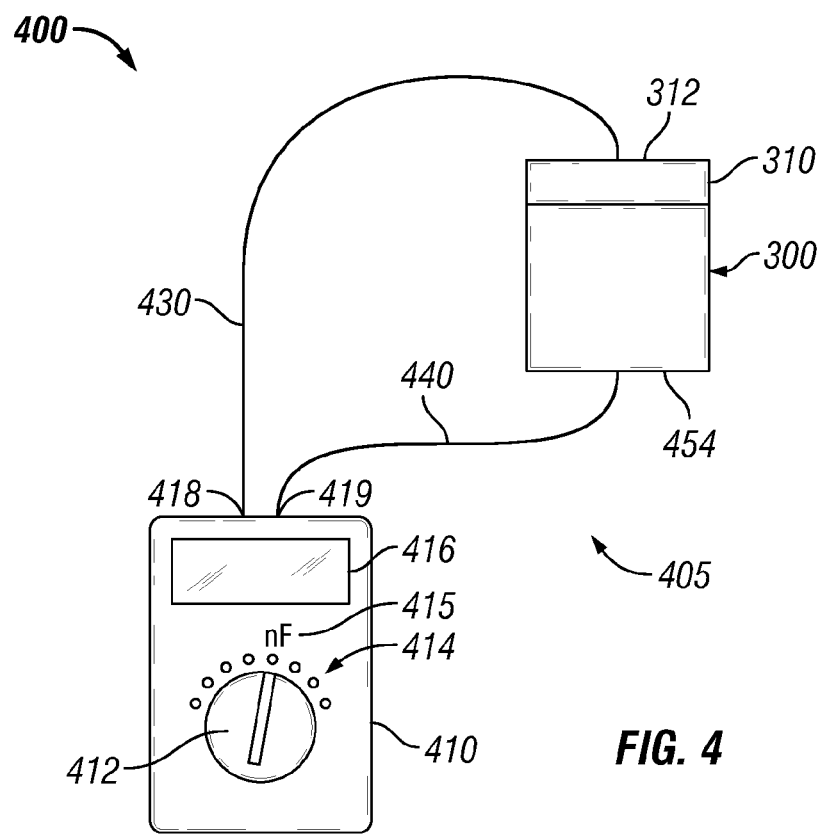
FIG. 4 is a schematic view of a capacitance measuring system in accordance to one exemplary embodiment of the present invention.

FIG. 4 is a schematic view of a capacitance measuring system 400 in accordance to one exemplary embodiment of the present invention. Referring to FIG. 4, the capacitance measuring system 400 includes a capacitance measuring device 410, the leached PDC cutter 300, a first wire 430, and a second wire 440. Although certain components have been enumerated as being included in the capacitance measuring system 400, additional components are included in other exemplary embodiments. Additionally, although the description provided below has been provided with respect to the leached PDC cutter 300, a different component, such as the PCD cutting table 310 alone or other component that includes another type of leached polycrystalline structure, is used in lieu of the leached PDC cutter 300. Additionally, although the description provided below has been provided with respect to the leached PDC cutter 300, a different component, such as a chemically cleaned leached PDC cutter (not shown), is used in lieu of the leached PDC cutter 300. The chemically cleaned leached PDC cutter has had at least a portion of the by-product materials 398 (FIG. 3) removed by using one or more processes described in related application entitled, "Method To Improve The Performance Of A Leached Cutter", which has been mentioned above and incorporated by reference herein. The leached PDC cutter 300 has been previously described with respect to FIG. 3 and is not repeated again herein for the sake of brevity.

The capacitance measuring device 410 is a device that measures the capacitance of an energy storage device, which is the leached PDC cutter 300 in the instant exemplary embodiment. Capacitance is a measure of the amount of electric potential energy stored, or separated, for a given electric potential. A common form of energy storage device is a parallel-plate capacitor. In the instant exemplary embodiment, the leached PDC cutter 300 is an example of the parallel-plate capacitor. The capacitance of the energy storage device is typically measured in farads, or nanofarads.

One example of the capacitance measuring device 410 is a multi-meter; however, other capacitance measuring devices known to people having ordinary skill in the art are used in one or more alternative exemplary embodiments. The multi-meter 410 includes a positionable dial 412, a plurality of measurement settings 414, a display 416, a positive terminal 418, and a negative terminal 419. According to some exemplary embodiments, the positionable dial 412 is rotatable in a clockwise and/or counter-clockwise manner and is set to one of several available measurement settings 414. In the instant exemplary embodiment, the positionable dial 412 is set to a nanofaraday setting 415 so that the multi-meter 410 measures capacitance values. The display 416 is fabricated using polycarbonate, glass, plastic, or other known suitable material and communicates a measurement value, such as a capacitance value, to a user (not shown) of the multi-meter 410. The positive terminal 418 is electrically coupled to one end of the first wire 430, while the negative terminal 419 is electrically coupled to one end of the second wire 440.

The first wire 430 is fabricated using a copper wire or some other suitable conducting material or alloy known to people having ordinary skill in the art. According to some exemplary embodiments, the first wire 430 also includes a non-conducting sheath (not shown) that surrounds the copper wire and extends from about one end of the copper wire to an opposing end of the cooper wire. The two ends of the copper wire are exposed and are not surrounded by the non-conducting sheath. In some exemplary embodiments, an insulating material (not shown) also surrounds the copper wire and is disposed between the copper wire and the non-conducting sheath. The insulating material extends from about one end of the non-conducting sheath to about an opposing end of the non-conducting sheath. As previously mentioned, one end of the first wire 430 is electrically coupled to the positive terminal 418, while the opposing end of the first wire 430 is electrically coupled to the cutting surface 312 of the leached PDC cutter 300. The opposing end of the first wire 430 is electrically coupled to the cutting surface 312 in one of several methods. In one example, the first wire 430 is electrically coupled to the cutting surface 312 using one or more fastening devices (not shown), such as a clamp, or using an equipment (not shown) that supplies a force to retain the first wire 430 in electrical contact with the cutting surface 312. In another example, a clamp (not shown) is coupled to the opposing end of the first wire 430 and a conducting component (not shown), such as aluminum foil, is coupled to, or placed in contact with, the cutting surface 312. The clamp is electrically coupled to the conducting component, thereby electrically coupling the first wire 430 to the cutting surface 312. Additional methods for coupling the first wire 430 to the cutting surface 312 can be used in other exemplary embodiments.

The second wire 440 is fabricated using a copper wire or some other suitable conducting material or alloy known to people having ordinary skill in the art. According to some exemplary embodiments, the second wire 440 also includes a non-conducting sheath (not shown) that surrounds the copper wire and extends from about one end of the copper wire to an opposing end of the cooper wire. The two ends of the copper wire are exposed and are not surrounded by the non-conducting sheath. In some exemplary embodiments, an insulating material (not shown) also surrounds the copper wire and is disposed between the copper wire and the non-conducting sheath. The insulating material extends from about one end of the non-conducting sheath to an opposing end of the non-conducting sheath. As previously mentioned, one end of the second wire 440 is electrically coupled to the negative terminal 419, while the opposing end of the second wire 440 is electrically coupled to a bottom surface 454, which is similar to the bottom surface 154 (FIG. 1), of the leached PDC cutter 300. The second wire 440 is electrically coupled to the bottom surface 454 in a similar manner as the first wire 430 is electrically coupled to the cutting surface 312.

Hence, a circuit 405 is completed using the multi-meter 410, the first wire 430, the leached PDC cutter 300, and the second wire 440. The current is able to flow from the positive terminal 418 of the multi-meter 410 to the cutting surface 312 of the leached PDC cutter 300 through the first wire 430. The current then flows through the leached PDC cutter 300 to the bottom surface 454 of the leached PDC cutter 300. When the multi-meter 410 is turned on, a voltage differential exists between the cutting surface 312 and the bottom surface 454. The current then flows from the bottom surface 454 to the negative terminal 419 of the multi-meter 410 through the second wire 440. The capacitance measurement of the leached PDC cutter 300 is determined when the value displayed on the display 416 reaches a peak value or remains constant for a period of time.

Figure 5:
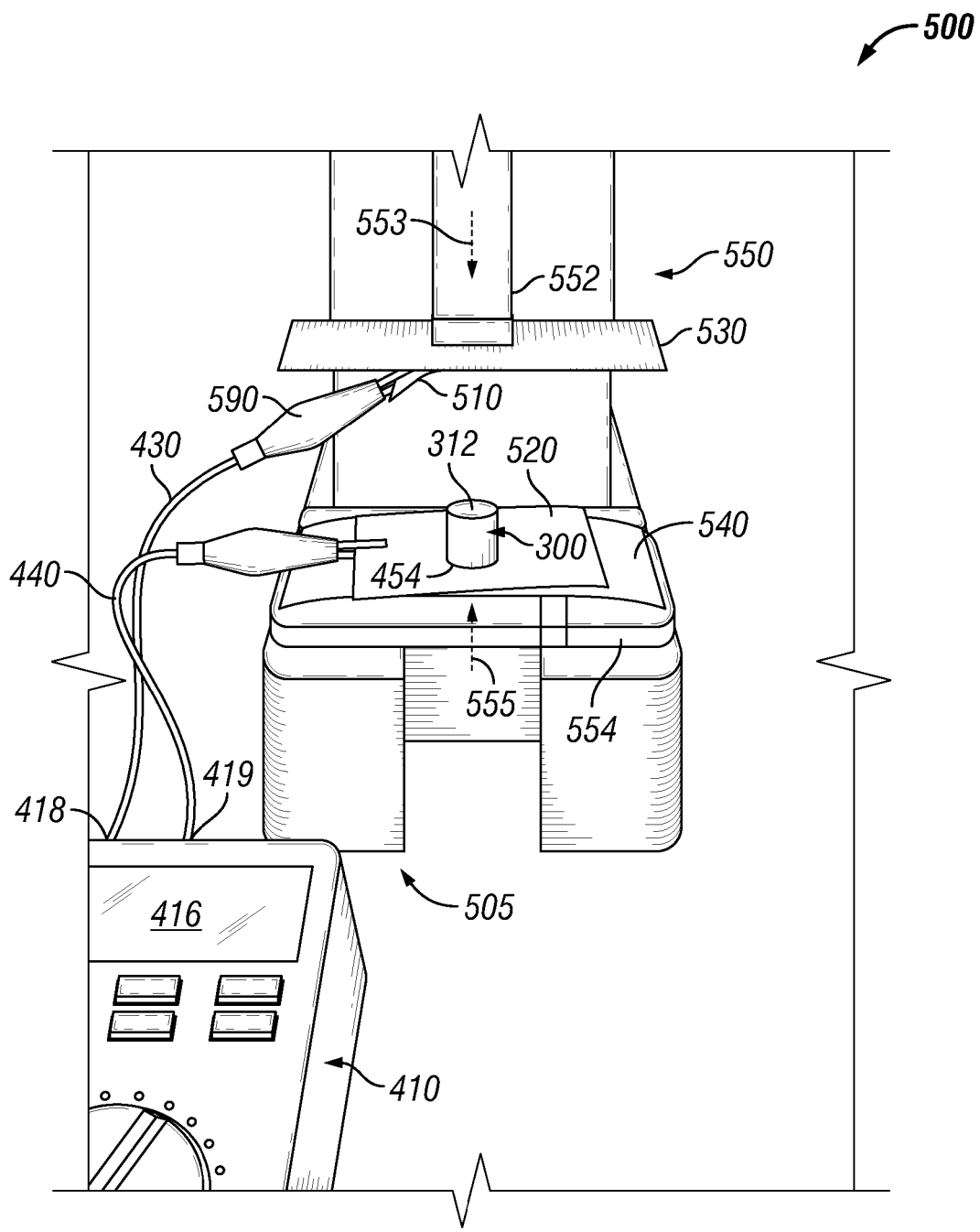
FIG. 5 is a schematic view of a capacitance measuring system in accordance to another exemplary embodiment of the present invention.

FIG. 5 is a schematic view of a capacitance measuring system 500 in accordance to another exemplary embodiment of the present invention. Referring to FIG. 5, the capacitance measuring system 500 includes the capacitance measuring device 410, the leached PDC cutter 300, the first wire 430, the second wire 440, a first conducting material 510, a second conducting material 520, a first insulating material 530, a second insulating material 540, and an Arbor Press 550. Although certain components have been enumerated as being included in the capacitance measuring system 500, additional components are included in other exemplary embodiments. Further, although certain components have been enumerated as being included in the capacitance measuring system 500, alternative components having similar functions as the enumerated components are used in alternative exemplary embodiments. Additionally, although the description provided below has been provided with respect to the leached PDC cutter 300, a different component, such as the PCD cutting table 310 (FIG. 3) alone or other component that includes another type of leached polycrystalline structure, is used in lieu of the leached PDC cutter 300. Additionally, although the description provided below has been provided with respect to the leached PDC cutter 300, a different component, such as the chemically cleaned leached PDC cutter mentioned above, is used in lieu of the leached PDC cutter 300. The capacitance measuring device 410, the leached PDC cutter 300, the first wire 430, and the second wire 440 have been previously described and are not repeated again herein for the sake of brevity.

The first conducting material 510 and the second conducting material 520 are similar to one another in certain exemplary embodiments, but are different in other exemplary embodiments. According to one exemplary embodiment, the conducting materials 510, 520 are fabricated using aluminum foil; however, other suitable conducting materials can be used. The first conducting material 510 is positioned adjacently above and in contact with the cutting surface 312. The second conducting material 520 is positioned adjacently below and in contact with the bottom surface 454. The first conducting material 510 and the second conducting material 520 provide an area to which the first wire 430 and the second wire 440, respectively, make electrical contact. Additionally, the first conducting material 510 and the second conducting material 520 assist in minimizing contact resistance with the cutting surface 312 and the bottom surface 454, respectively, which is discussed in further detail below. In certain exemplary embodiments, the first conducting material 510 and the second conducting material 520 are the same shape and size; while in other exemplary embodiments, one of the conducting materials 510, 520 is a different shape and/or size than the other conducting material 510, 520.

The first insulating material 530 and the second insulating material 540 are similar to one another in certain exemplary embodiments, but are different in other exemplary embodiments. According to one exemplary embodiment, the insulating materials 530, 540 are fabricated using paper; however, other suitable insulating materials, such as rubber, can be used. The first insulating material 530 is positioned adjacently above and in contact with the first conducting material 510. The second insulating material 540 is positioned adjacently below and in contact with the second conducting material 520. The first insulating material 530 and the second insulating material 540 provide a barrier to direct current flow only through a circuit 505, which is discussed in further detail below. In certain exemplary embodiments, the first insulating material 530 and the second insulating material 540 are the same shape and size; while in other exemplary embodiments, one of the insulating materials 530, 540 is a different shape and/or size than the other insulating material 530, 540. Additionally, in certain exemplary embodiments, the insulating materials 530, 540 is larger in size than its corresponding conducting material 510, 520. However, one or more of the insulating materials 530, 540 is either larger or smaller than its corresponding conducting material 510, 520 in alternative exemplary embodiments.

The Arbor Press 550 includes an upper plate 552 and a base plate 554. The upper plate 552 is positioned above the base plate 554 and is movable towards the base plate 554. In other exemplary embodiments, the base plate 554 is movable towards the upper plate 552. The first insulating material 530, the first conducting material 510, the leached PDC cutter 300, the second conducting material 520, and the second insulating material 540 are positioned between the upper plate 552 and the base plate 554 such that the second insulating material 540 is positioned adjacently above and in contact with the base plate 554. The upper plate 552 is moved towards the base plate 554 until the upper plate 552 applies a downward load 553 onto the cutting surface 312 of the leached PDC cutter 300. When the downward load 553 is applied, the first conducting material 510 is deformed and adapted to the rough and very stiff cutting surface 312, thereby minimizing contact resistance between the first conducting material 510 and the cutting surface 312 and greatly improving the capacitance measurement consistency. At this time, the base plate 554 also applies an upward load 555 onto the bottom surface 454 of the leached PDC cutter 300. When the upward load 555 is applied, the second conducting material 520 is deformed and adapted to the rough and very stiff bottom surface 454, thereby minimizing contact resistance between the second conducting material 520 and the bottom surface 454 and greatly improving the capacitance measurement consistency. In certain exemplary embodiments, the downward load 553 is equal to the upward load 555. The downward load 553 and the upward load 555 is about one hundred pounds; however, these loads 553, 555 range from about two pounds to about a critical load. The critical load is a load at which the leached PDC cutter 300 is damaged when applied thereto.

In one exemplary embodiment, the second insulating material 540 is positioned on the base plate 554, the second conducting material 520 is positioned on the second insulating material 540, the leached PDC cutter 300 is positioned on the second conducting material 520, the first conducting material 510 is positioned on the leached PDC cutter 300, and the first insulating material 530 is positioned on the first conducting material 510. The upper plate 552 is moved towards the first insulating material 530 until the downward load 553 is applied onto the leached PDC cutter 300. In an alternative exemplary embodiment, one or more components, such as the first insulating material 530 and the first conducting material 510, are coupled to the upper plate 552 prior to the upper plate 552 being moved towards the base plate 554. Although an Arbor Press 550 is used in the capacitance measuring system 500, other equipment capable of delivering equal and opposite loads to each of the cutting surface 312 and the bottom surface 454 of the leached PDC cutter 300 can be used in other exemplary embodiments.

One end of the first wire 430 is electrically coupled to the positive terminal 418 of the multi-meter 410, while the opposing end of the first wire 430 is electrically coupled to the first conducting material 510, which thereby becomes electrically coupled to the cutting surface 312 of the leached PDC cutter 300. In one exemplary embodiment, a clamp 590 is coupled to the opposing end of the first wire 430 which couples the first wire 430 to the first conducting material 510. One end of the second wire 440 is electrically coupled to the negative terminal 419 of the multi-meter 410, while the opposing end of the second wire 440 is electrically coupled to the second conducting material 520, which thereby becomes electrically coupled to the bottom surface 454 of the leached PDC cutter 300. In one exemplary embodiment, a clamp (not shown), similar to clamp 590, is coupled to the opposing end of the second wire 440, which couples the second wire 440 to the second conducting material 520. Hence, the circuit 505 is completed using the multi-meter 410, the first wire 430, the first conducting material 510, the leached PDC cutter 300, the second conducting material 520, and the second wire 440. The current is able to flow from the positive terminal 418 of the multi-meter 410 to the cutting surface 312 of the leached PDC cutter 300 through the first wire 430 and the first conducting material 510. The current then flows through the leached PDC cutter 300 to the bottom surface 454 of the leached PDC cutter 300. When the multi-meter 410 is turned on, a voltage differential exists between the cutting surface 312 and the bottom surface 454. The current then flows from the bottom surface 454 to the negative terminal 419 of the multi-meter 410 through the second conducting material 520 and the second wire 440. The first insulating material 530 and the second insulating material 540 prevent the current from flowing into the Arbor Press 550. The capacitance measurement of the leached PDC cutter 300 is determined when the value displayed on the display 416 reaches a peak value or remains constant for a period of time.

Figure 6:
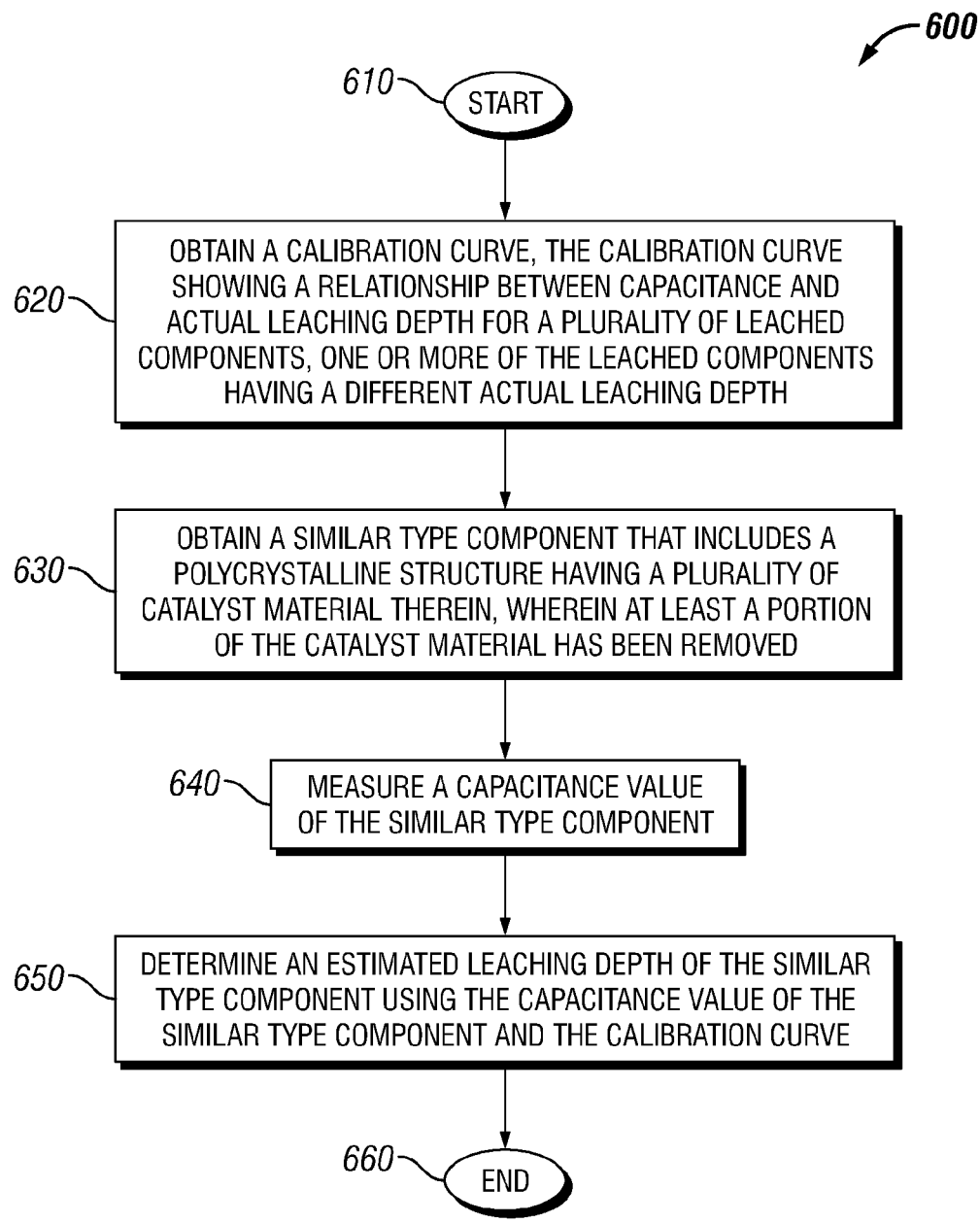
FIG. 6 is a flowchart depicting a non-destructive leaching depth estimation method in accordance with an exemplary embodiment of the present invention.

FIG. 6 is a flowchart depicting a non-destructive leaching depth estimation method 600 in accordance with an exemplary embodiment of the present invention. Although FIG. 6 shows a series of steps depicted in a certain order, the order of one or more steps can be rearranged, combined into fewer steps, and/or separated into more steps than that shown in other exemplary embodiments. Referring to FIG. 6, the non-destructive leaching depth estimation method 600 begins at step 610. Upon starting at step 610, the non-destructive leaching depth estimation method 600 proceeds to step 620. At step 620, a calibration curve is obtained. The calibration curve can be generated from tests or acquired from elsewhere.

Figure 7:
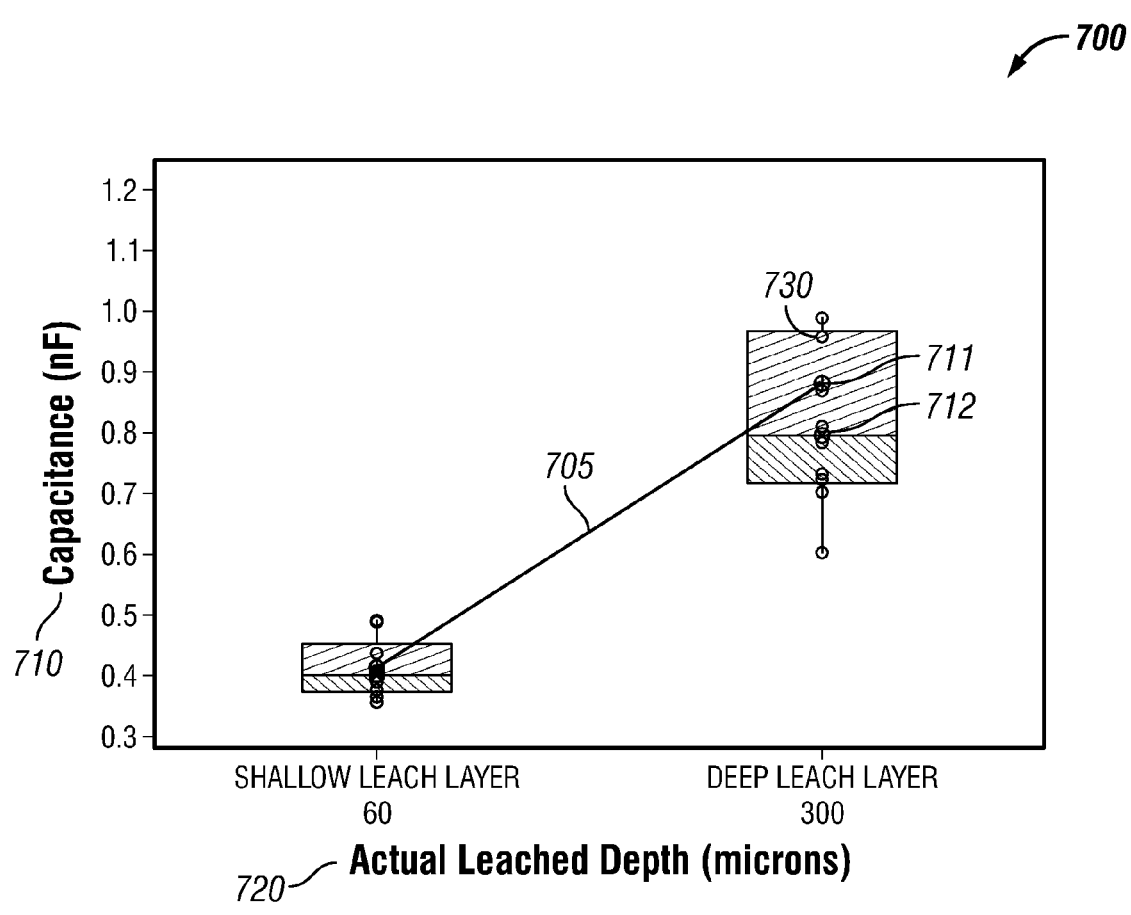
FIG. 7 is a graphical chart depicting a calibration curve that shows a relationship between capacitance and actual leaching depth for a plurality of leached components in accordance with an exemplary embodiment of the present invention.

FIG. 7 is a graphical chart 700 depicting the calibration curve 705 that shows a relationship between capacitance 710 and actual leaching depth 720 for a plurality of leached components 300 (FIG. 3) in accordance with an exemplary embodiment of the present invention. Referring to FIG. 7, one or more of the leached components 300 (FIG. 3) have a different actual leaching depth 720 than at least one other leached component 300 (FIG. 3). The leached component 300 (FIG. 3) is the leached PDC cutter 300 (FIG. 3) according to some exemplary embodiments; however, the leached component 300 can be only the PCD cutting table 310 (FIG. 3) or some other component that has a polycrystalline structure that has had at least some of the catalyst material removed from therein. Alternatively, in certain exemplary embodiments, the leached component 300 can be the chemically cleaned leached PDC cutter mentioned above.

The calibration curve 705 is generated by obtaining two or more leached components 300 (FIG. 3). The calibration curve 705 becomes more precise as more leached components 300 (FIG. 3) are used in generating the calibration curve 705. The capacitance data points 730 are obtained by measuring the capacitance 710 of each leached component 300 (FIG. 3). In certain exemplary embodiments, a plurality of capacitance data points 730 are obtained for each leached component 300 (FIG. 3). For example, the capacitance 710 is measured five times for each leached component 300 (FIG. 3). Obtaining a plurality of capacitance data points 730 for each leached component 300 (FIG. 3) improves the statistical significance of the capacitance data points 730 being collected. According to some exemplary embodiments, the leached component 300 (FIG. 3) is depolarized after each measurement for capacitance 710, before each measurement for capacitance 710, or before and after each measurement for capacitance 710. The leached component 300 is depolarized in one or a combination of different manners, such as grounding the leached component 300 (FIG. 3), wrapping the leached component 300 (FIG. 3) in aluminum foil or similar type material, heat treating the leached component 300 (FIG. 3), dropping the leached component 300 (FIG. 3) in a salt solution, or waiting to discharge the leached component 300 (FIG. 3). The leached component 300 (FIG. 3) is discharged by waiting about twenty-four hours, but the waiting time is greater or less in other exemplary embodiments. Depolarizing an object is known to people having ordinary skill in the art.

Once the capacitance 710 is measured for each leached component 300 (FIG. 3), the actual leaching depth 720 for each leached component 300 (FIG. 3) is determined. In some examples, the actual leaching depth 720 for a leached component 300 (FIG. 3) is determined by cutting the leached component 300 (FIG. 3), polishing the cut edge of the leached component 300 (FIG. 3), and visually measuring the actual leaching depth 720 under a magnifying device (not shown), such as a microscope. Although one method for determining the actual leaching depth 720 is described, other methods known to people having ordinary skill in the art can be used to determine the actual leaching depth 720 without departing from the scope and spirit of the exemplary embodiment. Each capacitance data point 730 is plotted on the graphical chart 700, where the actual leaching depth 720 is plotted versus the capacitance 710 that is measured. Once the capacitance data points 730 are plotted on the graphical chart 700, the calibration curve 705 is determined pursuant to methods known to people having ordinary skill in the art. For example, the calibration curve 705 is generated by using the average capacitance 711 of each leached component 300, the median capacitance 712 of each leached component, or by calculating the best fit curve. The best fit curve can be formed with a ninety-five percent confidence level, but this confidence level can range from about sixty percent to almost about one hundred percent, for example, 99.99 percent. The calibration curve 705 correlates the measured capacitance 710, which can be measured in nanofarads, with the actual leaching depth 720, which can be measured in microns. Although a few methods for generating the calibration curve 705 have been described, other methods, either destructive or non-destructive, can be used to generate the calibration curve 705.

According to FIG. 7, the actual leaching depth 720 is directly related to the capacitance 710. Thus, as the actual leaching depth 720 increases, the capacitance 710 that is measured also increases. Conversely, as the actual leaching depth 720 decreases, the capacitance 710 that is measured also decreases. Additionally, the data scattering, or range of measured capacitance 710, is greater as the actual leaching depth 720 increases. Although FIG. 7 shows a direct relationship between the actual leaching depth 720 and the capacitance 710; in actuality, the relationship between the capacitance 710 and the actual leaching depth 720 is an inverse relationship. The formula to calculate the capacitance 710 is:

$$C = \in_r (A/(4\pi d))$$

where
  C is the capacitance;
  A is the area of overlap of the two plates;
  $\in_r$ is the relative static permittivity (sometimes called the dielectric constant); and
  d is the separation between the plates.

Thus, as "d", or the actual leaching depth 720, increases, the capacitance 710 decreases, and visa versa. The opposite phenomena is occurring in FIG. 7 because the by-product materials 398 (FIG. 3) present with the leached layer 354 (Figure) becomes polarized during the measurements, and thus the relative static permittivity is not constant.

Therefore, in certain exemplary embodiments, the leached layer 354 is treated, such as by chemical treatment, to have at least a portion of the by-product materials 398 (FIG. 3) removed. This treatment is dependent upon the methods and/or chemicals used to leach the PCD cutting table 310 (FIG. 3). This treated leached PDC cutter is used within the capacitance measuring system 400, 500 or within some other capacitance measuring system in lieu of the leached PDC cutter 300 (FIG. 3). The calibration curve that is determined using the treated leached PDC cutters would show the relationship between the actual leaching depth 720 and the capacitance 710 being an inverse relationship. In the methods using the treated leached PDC cutter, which has had at least a portion of the by-product materials 398 (FIG. 3) removed, the de-polarizing step is optional.

Referring back to FIG. 6, the non-destructive leaching depth estimation method 600 proceeds to step 630. At step 630, a similar type component, similar to leached cutter 300, is obtained. However, if the calibration curve was determined using treated leached PDC cutters, the similar type component is a different treated leached PDC cutter where the actual leaching depth is desired to be ascertained. This similar type component includes a polycrystalline structure that has a plurality of catalyst material therein. At least a portion of this catalyst material has been removed. This removed portion has an unknown depth, which is the leaching depth. The non-destructive leaching depth estimation method 600 proceeds to step 640. At step 640, the capacitance of the similar type component is measured. According to some exemplary embodiment, this capacitance is measured using the capacitance measuring system 400 (FIG. 4) or the capacitance measuring system 500 (FIG. 5). The non-destructive leaching depth estimation method 600 proceeds to step 650. At step 650, the estimated leaching depth of the similar type component is determined using the capacitance of the similar type component and the calibration curve 705 (FIG. 7). The estimated leaching depth is an estimation of the actual leaching depth and ranges from about one micron to about fifty microns from the actual leaching depth. The non-destructive leaching depth estimation method 600 proceeds to step 660, where the non-destructive leaching depth estimation method 600 ends.

Figure 8:
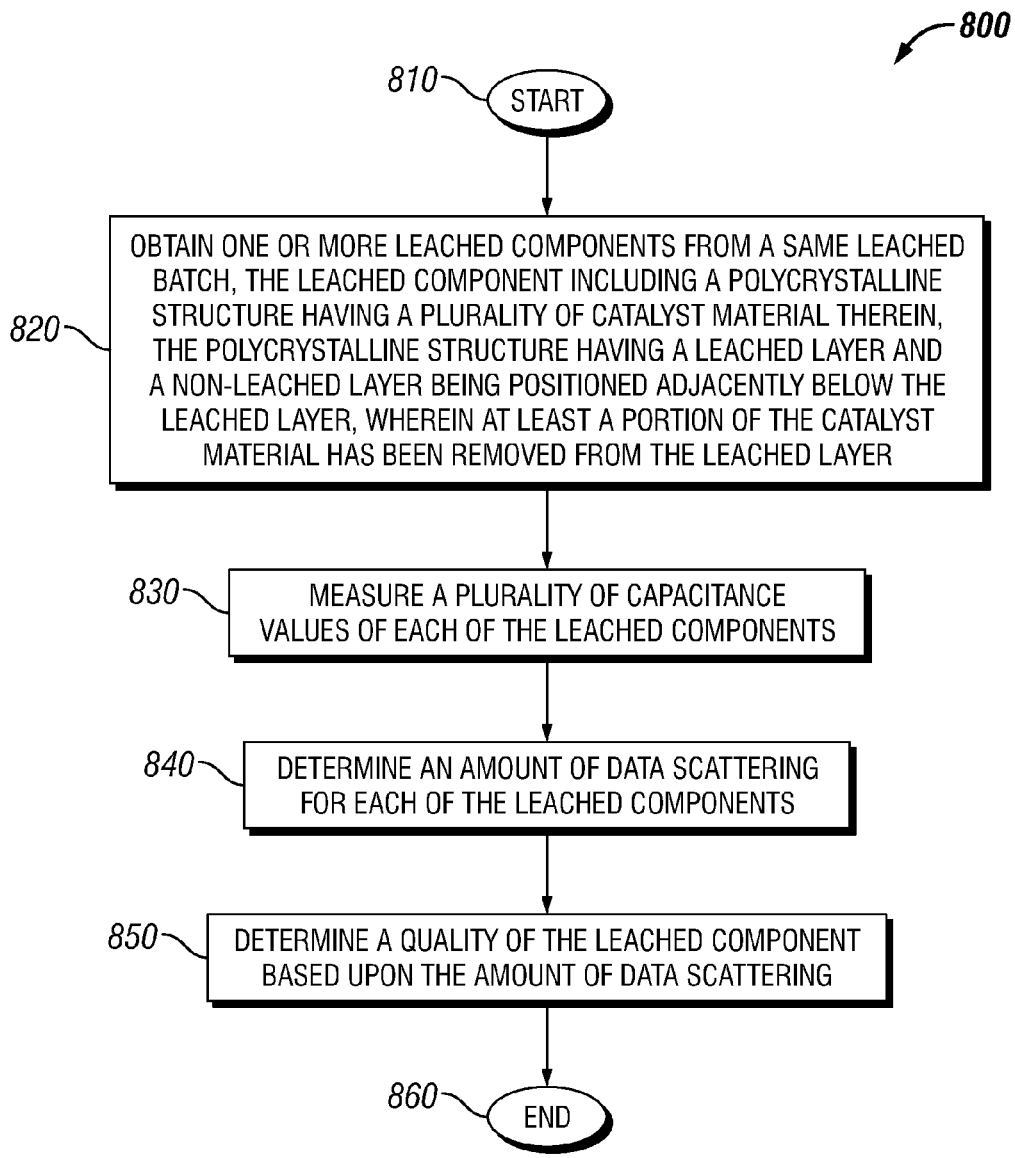
FIG. 8 is a flowchart depicting a microstructural quality determination method in accordance with an exemplary embodiment of the present invention.

FIG. 8 is a flowchart depicting a microstructural quality determination method 800 in accordance with an exemplary embodiment of the present invention. Although FIG. 8 shows a series of steps depicted in a certain order, the order of one or more steps can be rearranged, combined into fewer steps, and/or separated into more steps than that shown in other exemplary embodiments. Referring to FIG. 8, the microstructural quality determination method 800 begins at step 810. Upon starting at step 810, the microstructural quality determination method 800 proceeds to step 820. At step 820, one or more leached components that include a polycrystalline structure is obtained from a same leached batch. The same leached batch is a group of components that were leached in the same leaching process at the same time. The polycrystalline structure includes a leached layer and a non-leached layer being positioned adjacently below the leached layer. The non-leached layer includes a plurality of catalyst material therein, while the leached layer has had at least a portion of the catalyst material removed. The microstructural quality determination method 800 proceeds to step 830. At step 830, a plurality of capacitance values are measured for each of the leached components. The capacitance values are determined using the capacitance measuring system 400 (FIG. 4) or the capacitance measuring system 500 (FIG. 5). The microstructural quality determination method 800 proceeds to step 840. At step 840, an amount of data scattering is determined for each leached component. The amount of data scattering for a leached component is determined by a differential between the highest measured capacitance and the lowest measured capacitance for that leached component and by statistical results of where each measured capacitance lies. The microstructural quality determination method 800 proceeds to step 850. At step 850, a quality of the leached component is determined based upon the amount of data scattering. The quality of the leached component relates to the microstructural quality and/or the leaching quality. The microstructural quality relates to the porosity of the microstructure. The microstructural quality is a good quality when there is low porosity. Conversely, the microstructural quality is a poor quality when there is high porosity. The leaching quality is a good quality when there is less catalyst materials present within the leached layer of the polycrystalline structure. Conversely, the leaching quality is a poor quality when there is more catalyst materials present within the leached layer of the polycrystalline structure. In some exemplary embodiments, the quality of the leached component is considered to be good when the amount of data scattering is determined to be small. Conversely, the quality of the leached component is considered to be poor when the amount of data scattering is determined to be large. The relative terms of small and large are determined when comparing the data scattering of a first leached component to the data scattering of a second leached component that was leached in the same batch as the first leached component.

Figure 9:
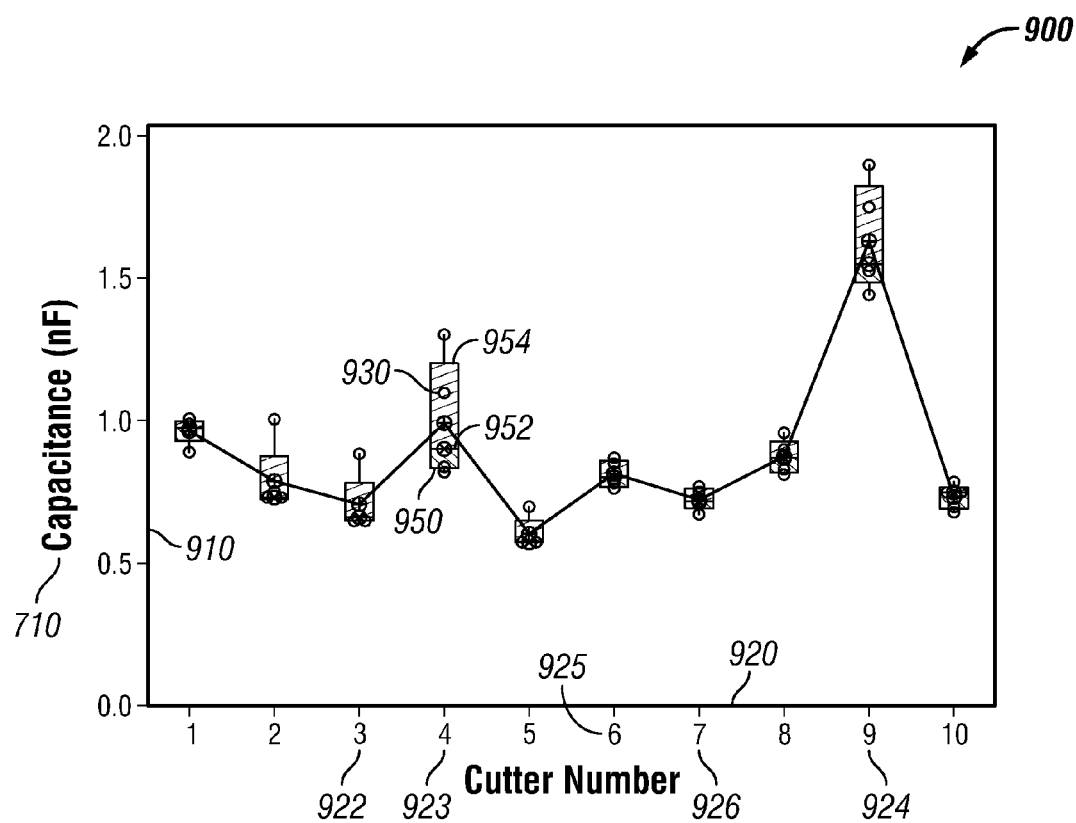
FIG. 9 is a data scattering chart that shows the measured capacitance for a plurality of cutters in accordance with an exemplary embodiment of the present invention.

FIG. 9 is a data scattering chart 900 that shows the measured capacitance 710 for a plurality of leached cutters 922 from a same leaching batch in accordance with an exemplary embodiment of the present invention. Referring to FIG. 9, the data scattering chart 900 includes a cutter number axis 920 and a capacitance axis 910. The cutter number axis 920 includes the number of the cutters 922 tested. The capacitance axis 910 includes values for the measured capacitance 710. A capacitance data point 930 is obtained by measuring the capacitance of the cutter 922, or leached component 922, using the capacitance measuring system 400 (FIG. 4), the capacitance measuring system 500 (FIG. 5), or a similar type system. Each capacitance data point 930 is plotted on the data scattering chart 900. Each leached component 922 has its capacitance measured a plurality of times. In some exemplary embodiments, five capacitance data points 930 are obtained for each leached component 922, however, the number of measurements is greater or fewer in other exemplary embodiments. In some exemplary embodiments, a twenty-five percentile marking 950, a fifty percentile marking 952 (or average), and a seventy-five percentile marking 954 is shown in the chart 900 for each leached component 922. The area between the twenty-five percentile marking 950 and the seventy-five percentile marking 954 is shaded. The amount of data scattering is ascertained using this data scattering chart 900 and can be one or more of a differential between the highest and lowest capacitance measurements 710 for each leached component 922, a range between the twenty-five percentile marking 950 and the seventy-five percentile marking 954, or some similar observation made from the data scattering chart 900.

According to FIG. 9, cutter number 4 923 and cutter number 9 924 have a larger data scattering than for example cutter number 6 925 or cutter number 7 926. Hence, cutter number 4 923 and cutter number 9 924 have a poor leaching quality and/or a poor microstructural quality within the polycrystalline structure. The increase in amount of catalyst material within the polycrystalline structure causes this data scattering.

There are several benefits for non-destructively determining the leaching depth in an ultra-hard polycrystalline structure and/or characterizing at least a portion of the ultra-hard polycrystalline structure. For example, capacitance measurements can be made on all PDC cutters that are to be mounted and used in a tool, such as a drill bit, thereby being able to estimate the leaching depth in the ultra-hard polycrystalline structure included in the PDC cutter and/or characterizing at least a portion of the ultra-hard polycrystalline structure, such as the quality of the leaching and/or the quality of the microstructure. Hence, only certain PDC cutters are chosen to be mounted to the drill bit or other downhole tool. In another example, when a quantity of PDC cutters being leached within the same leaching batch are provided, such as one thousand PDC cutters, the capacitance of the PDC cutters are measured pursuant to the descriptions provided above. The PDC cutters that meet a desired quality and/or leaching depth are kept while the remaining PDC cutters that do not meet the desired leaching depth and/or quality are returned. Thus, in one exemplary embodiment, although one thousand PDC cutters being leached from the same batch are provided, two hundred PDC cutters, or twenty percent, may be retained while the remaining are returned. Thus, only the higher quality and/or the proper leaching depth PDC cutters are paid for and retained, which results in the PDC cutters performing better during their application.

Figure 10:
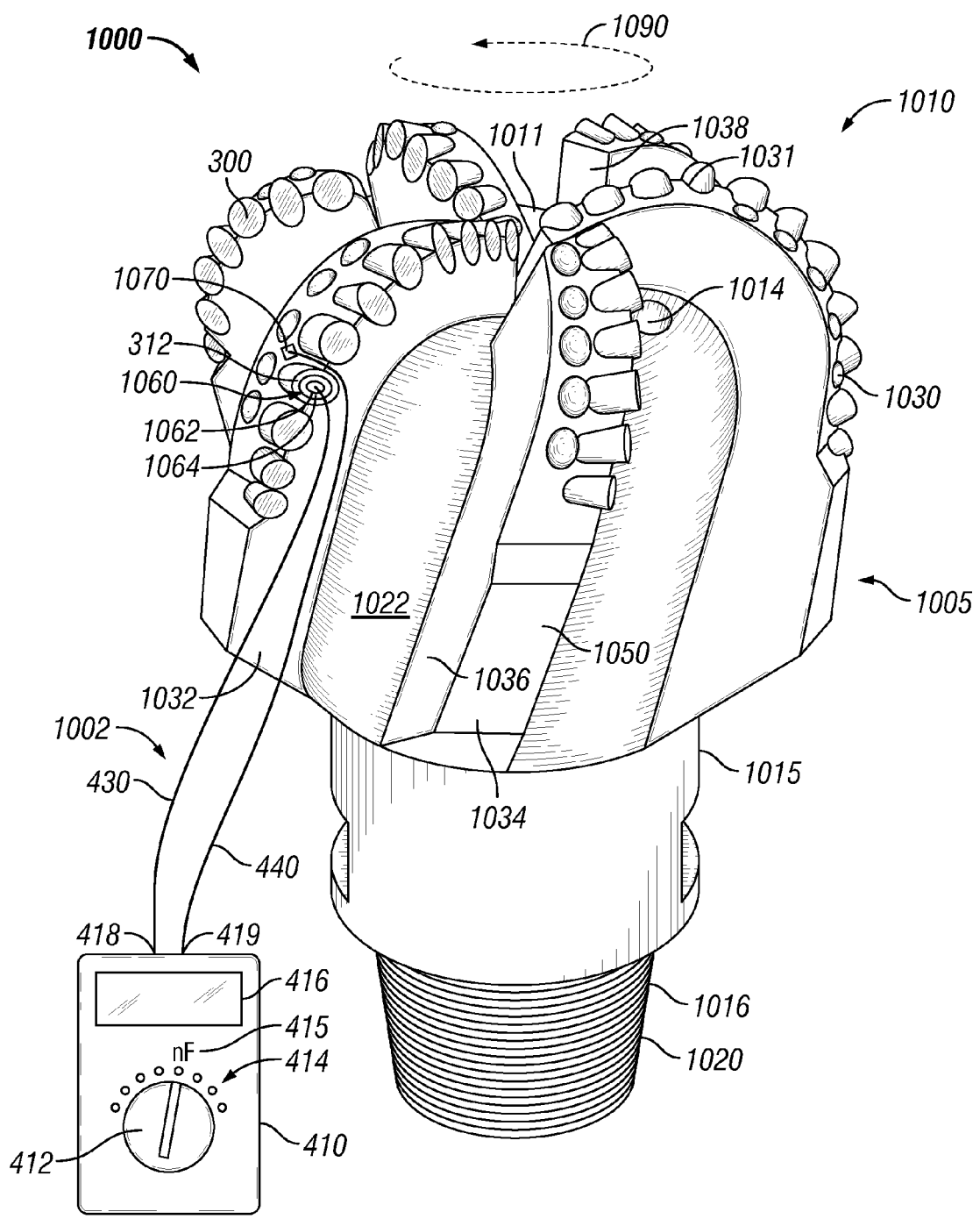
FIG. 10 is a schematic view of a capacitance measuring system in accordance with yet another exemplary embodiment of the present invention.

FIG. 10 is a schematic view of a capacitance measuring system 1000 in accordance to yet another exemplary embodiment of the present invention. Referring to FIG. 10, the capacitance measuring system 1000 includes the capacitance measuring device 410, a drill bit 1010 having at least one leached PDC cutter 300 coupled thereto, the first wire 430, and the second wire 440. Further, according to certain exemplary embodiments, the capacitance measuring system 1000 also includes a first conductive component 1060 and a second conductive component 1070. Although the drill bit 1010 has been enumerated as being part of the capacitance measuring system 1000, any tool, for example, a downhole tool, having at least one leached PDC cutter 300 is part of the capacitance measuring system 1000 in lieu of the drill bit 1010. Although certain components have been enumerated as being included in the capacitance measuring system 1000, additional components are included in other exemplary embodiments. Additionally, although the description provided below has been provided with respect to the leached PDC cutter 300, a different component, such as the PCD cutting table 310 (FIG. 3) alone or other component that includes another type of leached polycrystalline structure, is used in lieu of the leached PDC cutter 300. Additionally, although the description provided below has been provided with respect to the leached PDC cutter 300, a different component, such as a chemically cleaned leached PDC cutter (not shown), is used in lieu of the leached PDC cutter 300. The chemically cleaned leached PDC cutter has had at least a portion of the by-product materials 398 (FIG. 3) removed by using one or more processes described in a related application entitled, "Method To Improve The Performance Of A Leached Cutter", which has been mentioned above and incorporated by reference herein. The capacitance measuring device 410, the first wire 430, the second wire 440, and the leached PDC cutter 300 have been previously described with respect to FIGS. 3 and 4 and are therefore not repeated again in detail herein for the sake of brevity.

The drill bit 1010 includes a bit body 1005 that is coupled to a shank 1015 and is designed to rotate in a counter-clockwise direction 1090. The drill bit 1010 is fabricated using matrix material, machined steel, or any other suitable material or combination of materials that are known to people having ordinary skill in the art. The shank 1015 includes a threaded connection 1016 at one end 1020. The threaded connection 1016 couples to a drill string (not shown) or some other equipment that is coupled to the drill string. The threaded connection 1016 is shown to be positioned on the exterior surface of the one end 1020. This positioning assumes that the drill bit 1010 is coupled to a corresponding threaded connection located on the interior surface of a drill string (not shown). However, the threaded connection 1016 at the one end 1020 is alternatively positioned on the interior surface of the one end 1020 if the corresponding threaded connection of the drill string (not shown) is positioned on its exterior surface in other exemplary embodiments. A bore (not shown) is formed longitudinally through the shank 1015 and a plenum (not shown) is formed within the bit body 1005. The bore communicates drilling fluid from within the drill string to the plenum, which then communicates the drilling fluid to a drill bit face 1011, on the exterior surface of the drill bit 1010, via one or more nozzles 1014 during drilling operations. A flowpath (not shown) is formed within the bit body 1005 and extends from the plenum to the nozzle 1014. Typically, the flowpaths are formed via machining and/or using displacements that are known to people having ordinary skill in the art.

The bit body 1005 includes a plurality of gauge sections 1050, according to certain exemplary embodiments, and a plurality of blades 1030 extending from the drill bit face 1011 of the bit body 1005 towards the threaded connection 1016, where each blade 1030 extends to and terminates at a respective gauge section 1050. The blade 1030 and the respective gauge section 1050 are formed as a single component, but are formed separately in certain drill bits 1010. The drill bit face 1011 is positioned at one end of the bit body 1005 furthest away from the shank 1015. The plurality of blades 1030 form the cutting surface of the drill bit 1010. One or more of these plurality of blades 1030 are either coupled to the bit body 1005 or are integrally formed with the bit body 1005. The gauge sections 1050 are positioned at an end of the bit body 1005 adjacent the shank 1015. The gauge section 1050 includes one or more gauge cutters (not shown) in certain drill bits 1010. The gauge sections 1050 typically define and hold the full hole diameter of the drilled hole.

Each of the blades 1030 and gauge sections 1050 include a leading edge section 1032, a face section 1034, a trailing edge section 1036, and an inner section 1038. The face section 1034 extends from one longitudinal end of the trailing edge section 1036 to a longitudinal end of the leading edge section 1032. The leading edge section 1032 faces in the direction of rotation 1090, while the trailing edge section 1036 faces oppositely from the direction of rotation 1090. The inner section 1038 extends from one latitudinal end of the trailing edge section 1036 to a latitudinal end of the leading edge section 1032 and from the drill bit face 1011 to an end of the face section 1034. A junk slot 1022 is formed between each consecutive blade 1030, which allows for cuttings and drilling fluid to return to the surface of the wellbore (not shown) once the drilling fluid is discharged from the nozzles 1014. Each blade 1030 also includes one or more cutter pockets 1031 configured to receive a corresponding cutter 300, where at least one of the cutters 300 is a leached PDC cutter 300.

A plurality of cutters 300, where at least one of the cutters 300 is a leached PDC cutter 300, are coupled to each of the blades 1030 and extend outwardly from the surface of the blades 1030 to cut through earth formations when the drill bit 1010 is rotated during drilling. Although a leached PDC cutter 300 is used as one of the cutters 300, other types of cutters having a leached polycrystalline structure are contemplated as being used within the drill bit 1010. The cutters 300 and portions of the bit body 1005 deform the earth formation by scraping and/or shearing depending upon the type of drill bit 1010. Although one embodiment of the drill bit has been described, other configurations of drill bit embodiments or other downhole tools, which are known to people having ordinary skill in the art, are applicable to exemplary embodiments of the present invention. The cutters 300 are coupled to the drill bit 3010 via a brazing technique or some other known technique. During this coupling process, the leached PDC cutters 300 may have properties altered due to being exposed to high temperatures for a certain time period. Changing of the depth 353 (FIG. 3) of the leached layer 354 (FIG. 3) during the coupling process affects the properties of the leached PDC cutter 300.

The capacitance measuring device 410 includes the positionable dial 412, a plurality of measurement settings 414, the display 416, the positive terminal 418, and the negative terminal 419 according to certain exemplary embodiments. The positionable dial 412 is positioned to the nanofaraday setting 415 so that the capacitance measuring device 410, or multi-meter 410, measures capacitance values. These components have been previously been described and therefore are not repeated again herein for the sake of brevity. According to certain exemplary embodiments, the capacitance measuring device 410 includes a variable testing frequency that allows for capacitance measurements at different test frequencies. A second dial (not shown) or switch (not shown) may be included within the capacitance measuring device 410 to select the test frequency. According to some exemplary embodiments, the test frequency is variable from 100 kHz to 10 MHz, however, this frequency range is larger or smaller depending upon the testing requirements.

The first conductive component 1060 is coupled to the cutting surface 312 of the leached PDC cutter 300. According to some exemplary embodiments, the first conductive component 1060 includes a conductive portion 1062 that is in contact with the cutting surface 312. The surface of the conductive portion 1062 in contact with the cutting surface 312 is substantially planar according to some exemplary embodiments. According to some exemplary embodiments, the first conductive component 1060 includes an insulator 1064 surrounding the circumference, or perimeter, of the conductive portion 1062. In these exemplary embodiments, the insulator 1064 serves to reduce short circuiting when capacitance measurements are made on the leached PDC cutter 300 that has already been coupled to the drill bit 1010. In some exemplary embodiments, the first conductive component 1060 is cylindrically shaped and has a circular profile, however the profile may be of other geometric or non-geometric shapes. Yet, in other exemplary embodiments, the first conductive component 1060 is annularly shaped and optionally includes an insulator 1064 along the interior circumference, or perimeter, as well as along the exterior circumference, or perimeter. In yet other exemplary embodiments, the first conductive component 1060 is a tape or foil that is fabricated using a conductive material, such as copper, aluminum, some other metal or metal alloy. A pressure may be applied onto the first conductive component 1060 so that the contact with the cutting surface 312 is maintained and constant during the capacitance measurement.

The second conductive component 1070 is coupled to the blade 1030 of the drill bit 1010 and is positioned adjacent the leached PDC cutter 300 that is being tested according to some exemplary embodiments. According to other exemplary embodiments, the second conductive component 1070 is positioned elsewhere along the drill bit 1010. According to some exemplary embodiments, the second conductive component 1070 is a tape or foil that is fabricated using a conductive material, such as copper, aluminum, some other metal or metal alloy. A pressure may be applied onto the second conductive component 1070 so that the contact with the drill bit 1010 is maintained and constant during the capacitance measurement. In yet other exemplary embodiments, the second conductive component 1070 is similar to any of the other embodiments described with respect to the first conductive component 1060. According to some exemplary embodiments, the first and second conductive components 1060, 1070 are the same, while in other exemplary embodiments, the first and second conductive components 1060, 1070 are different from one another. In other exemplary embodiments, any conductive component may be used as the second conductive component 1070.

The first wire 430 has been previously described and therefore is not described again in detail for the sake of brevity. One end of the first wire 430 is electrically coupled to the positive terminal 418, while the opposing end of the first wire 430 is electrically coupled to the cutting surface 312 of the leached PDC cutter 300 via the first conductive component 1060. The opposing end of the first wire 430 is electrically coupled to the conductive portion 1062 of the first conductive component 1060 in one of several methods. In one example, the first wire 430 is electrically coupled to the conductive portion 1062 using one or more fastening devices (not shown), such as a clamp, or using an equipment (not shown) that supplies a force to retain the first wire 430 in electrical contact with the conductive portion 1062. The clamp is electrically coupled to the conductive portion 1062, thereby electrically coupling the first wire 430 to the cutting surface 312. Additional methods for coupling the first wire 430 to the conductive portion 1062 that are known to people having ordinary skill in the art can be used in other exemplary embodiments.

The second wire 440 has been previously described and therefore is not described again in detail for the sake of brevity. One end of the second wire 440 is electrically coupled to the negative terminal 419, while the opposing end of the second wire 440 is electrically coupled to the second conductive component 1070. The second wire 440 is electrically coupled to the second conductive component 1070 in a similar manner as the first wire 430 is electrically coupled to the conductive portion 1062. Additional methods for coupling the second wire 440 to the second conductive component 1070 that are known to people having ordinary skill in the art can be used in other exemplary embodiments.

Hence, a circuit 1002 is completed using the capacitance measuring device 410, the first wire 430, the leached PDC cutter 300 that is coupled to the drill bit 1010, the drill bit 1010, and the second wire 440. The current is able to flow from the positive terminal 418 of the capacitance measuring device 410 to the cutting surface 312 of the leached PDC cutter 300 through the first wire 430 and the first conductive component 1060. The current then flows through the leached PDC cutter 300 to the blade 1030, or bit body 1005, and into the second conductive component 1070. When the capacitance measuring device 410 is turned on, a voltage differential exists between the cutting surface 312 and the blade 1030, or bit body 1005. The current then flows from the blade 1030, or bit body 1005, to the negative terminal 419 of the capacitance measuring device 410 through the second wire 440. The capacitance measurement of the leached PDC cutter 300 is determined when the value displayed on the display 416 reaches a low peak value as the frequency is varied. Obtaining data when varying the frequency, or performing impedance spectroscopy or frequency sweeping, reduces noise in the measurement data.

Figure 11:
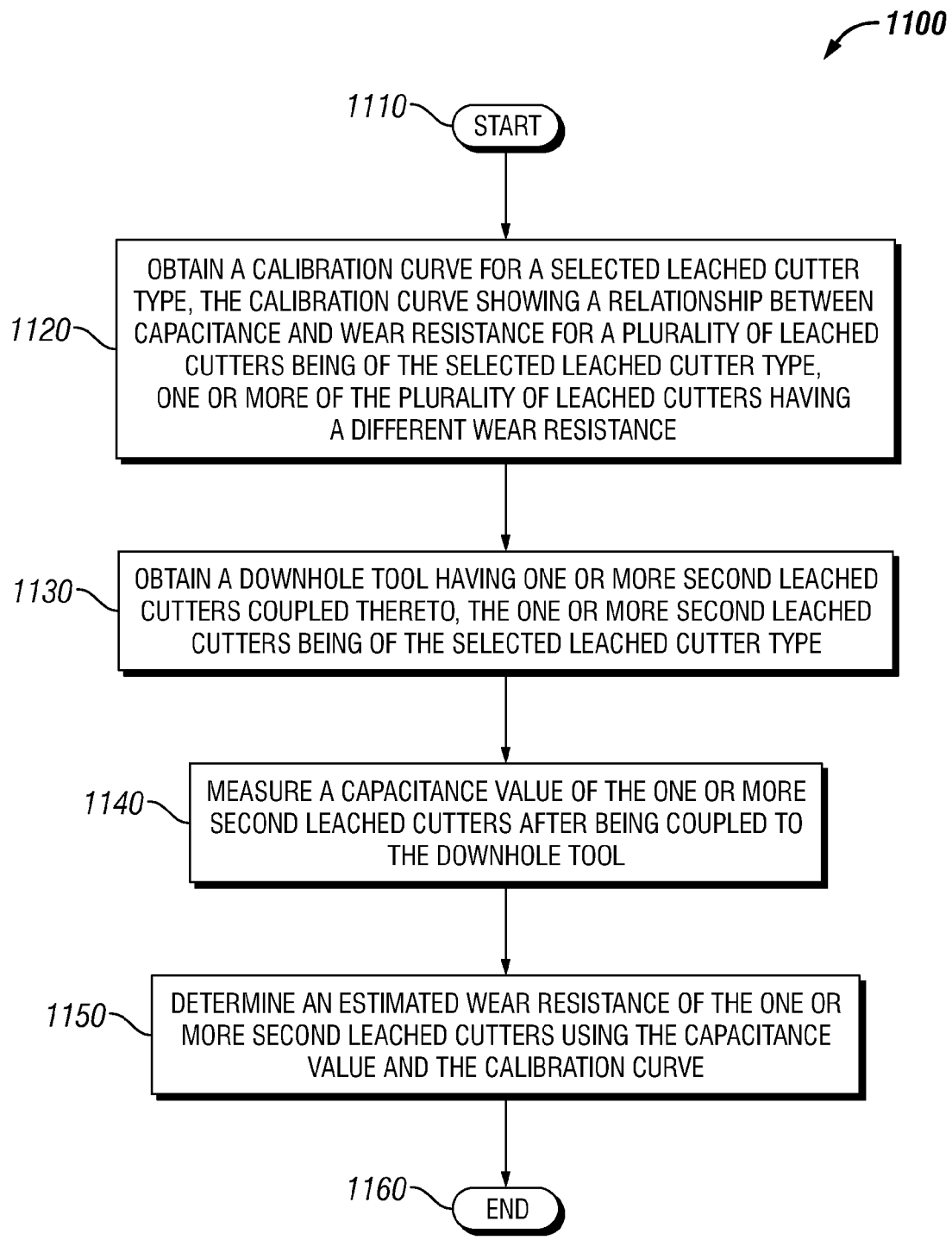
FIG. 11 is a flowchart depicting a non-destructive wear resistance estimation method in accordance with an exemplary embodiment of the present invention.

FIG. 11 is a flowchart depicting a non-destructive wear resistance estimation method 1100 in accordance with an exemplary embodiment of the present invention. Although FIG. 11 shows a series of steps depicted in a certain order, the order of one or more steps can be rearranged, combined into fewer steps, and/or separated into more steps than that shown in other exemplary embodiments. Referring to FIG. 11, the non-destructive wear resistance estimation method 1100 begins at step 1110. Upon starting at step 1110, the non-destructive wear resistance estimation method 1100 proceeds to step 1120. At step 1120, a calibration curve is obtained. The calibration curve can be generated from tests or acquired from elsewhere. The calibration curve is for a selected leached cutter type and shows a relationship between capacitance and wear resistance for a plurality of leached cutters being of the selected leached cutter type. One or more of the plurality of leached cutters have a different wear resistance, and thus a different capacitance measurement.

Although not illustrated, the calibration curved used in the non-destructive wear resistance estimation method 1100 is similar to the graphical chart 700 (FIG. 7) that depicts the calibration curve 705 (FIG. 7) which shows the relationship between capacitance 710 (FIG. 7) and actual leaching depth 720 (FIG. 7) for a plurality of leached components 300 (FIG. 3), except that this calibration curve shows the relationship of capacitance with wear resistance instead of actual leaching depth 720 (FIG. 7).

The calibration curve is generated by obtaining two or more leached components 300 (FIG. 3) of the same cutter type. The calibration curve becomes more precise as more leached components 300 (FIG. 3) are used in generating the calibration curve. The capacitance data points are obtained by measuring the capacitance 710 of each leached component 300 (FIG. 3). The method for determining the capacitance is described in more detail in conjunction with the description provided for FIG. 13 below. In certain exemplary embodiments, a plurality of capacitance data points, or measurements, are obtained for each leached component 300 (FIG. 3). For example, the capacitance is measured five times for each leached component 300 (FIG. 3). Obtaining a plurality of capacitance data points for each leached component 300 (FIG. 3) improves the statistical significance of the capacitance data points being collected. According to some exemplary embodiments, the leached component 300 (FIG. 3) is depolarized after each measurement for capacitance, before each measurement for capacitance, or before and after each measurement for capacitance. The leached component 300 is depolarized in one or a combination of different manners, such as grounding the leached component 300 (FIG. 3), wrapping the leached component 300 (FIG. 3) in aluminum foil or similar type material, heat treating the leached component 300 (FIG. 3), dropping the leached component 300 (FIG. 3) in a salt solution, or waiting to discharge the leached component 300 (FIG. 3). The leached component 300 (FIG. 3) is discharged by waiting about twenty-four hours, but the waiting time is greater or less in other exemplary embodiments. Depolarizing an object is known to people having ordinary skill in the art.

Once the capacitance is measured for each leached component 300 (FIG. 3), the wear resistance for each leached component 300 (FIG. 3) is determined. In some examples, the wear resistance for each of the leached components 300 (FIG. 3) is determined by using a VTL test, a granite log test, or any other test known to people having ordinary skill in the art. Each capacitance data point is plotted on a graphical chart (not shown), where the wear resistance is plotted versus the capacitance that is measured. Once the capacitance data points and the corresponding wear resistance data points are plotted on the graphical chart for each leached cutter 300 (FIG. 3), the calibration curve is determined pursuant to methods known to people having ordinary skill in the art. For example, the calibration curve is generated by using the average capacitance of each leached component 300 (FIG. 3), the median capacitance of each leached component 300 (FIG. 3), or by calculating the best fit curve. The best fit curve can be formed with a ninety-five percent confidence level, but this confidence level can range from about sixty percent to almost about one hundred percent, for example, 99.99 percent. The calibration curve correlates the measured capacitance, which can be measured in nanofarads, with the wear resistance. Although a few methods for generating the calibration curve have been described, other methods, either destructive or non-destructive, can be used to generate the calibration curve.

Figure 12:
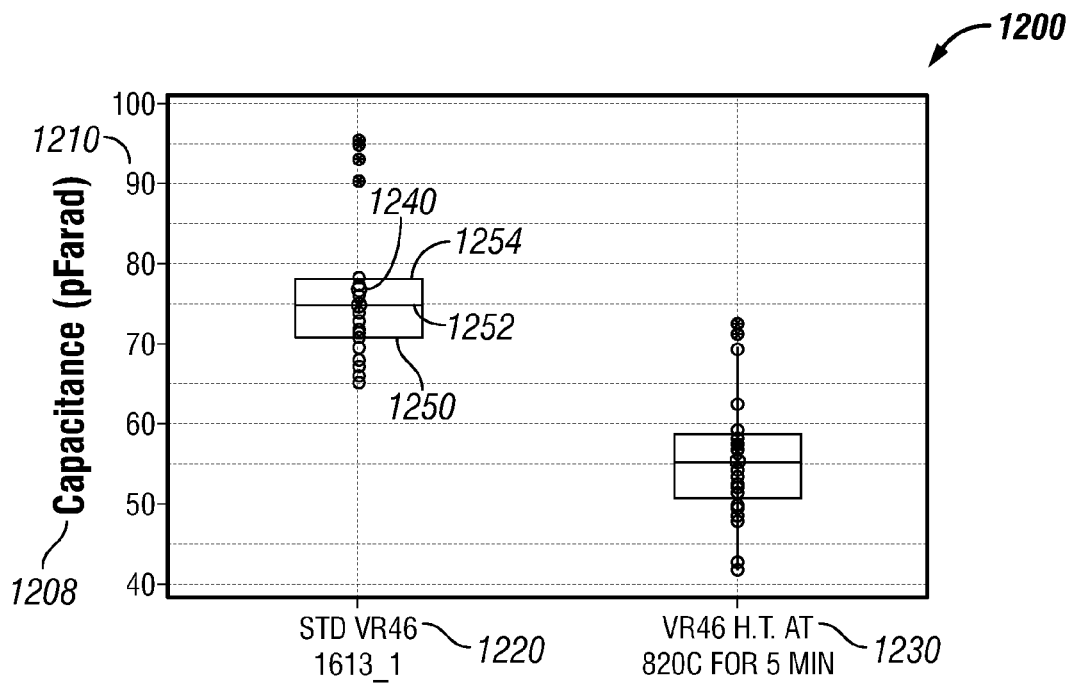
FIG. 12 is a graphical chart showing a measured capacitance value of a leached cutter prior to being affected by a heat treatment and a second leached cutter that has been affected by a heat treatment in accordance with an exemplary embodiment of the present invention.

Continuing reference to FIG. 11, the non-destructive wear resistance estimation method 1100 proceeds to step 1130. At step 1130, a downhole tool having one or more second leached cutters coupled thereto is obtained. The one or more second leached cutters are similar to the selected leached cutter type used in generating the calibration curve of step 1120, except that they have been coupled to the downhole tool, such as by a brazing process. It is these one or more second leached cutters where the wear resistance is desired to be ascertained. The non-destructive wear resistance estimation method 1100 proceeds to step 1140. At step 1140, the capacitance value of the one or more second leached cutters are measured. As previously mentioned, these second leached cutters have already been coupled to the downhole tool, such as by a brazing process. According to some exemplary embodiment, this capacitance value is measured using the capacitance measuring system 1000 (FIG. 10). One example of how the capacitance of a cutter has been affected is illustrated in FIG. 12, which is described in further detail below. The non-destructive wear resistance estimation method 1110 proceeds to step 1150. At step 1150, the estimated wear resistance of the one or more second leached cutters is determined using the capacitance value of the one or more second leached cutters and the calibration curve obtained in step 1110. The estimated wear resistance is an estimation of the actual wear resistance of the one or more second leached cutters. The non-destructive wear resistance estimation method 1100 proceeds to step 1160, where the non-destructive wear resistance estimation method 1100 ends.

FIG. 12 is a graphical chart 1200 showing a measured capacitance value 1210 of a leached cutter 1220 without any heat treatment and a second leached cutter 1230 that has been affected by a heat treatment in accordance with an exemplary embodiment of the present invention. Referring to FIG. 12, the graphical chart 1200 includes a cutter type heat treatment axis 1215 and a capacitance axis 1208. The cutter type heat treatment axis 1215 includes the leached cutter 1220 and the second leached cutter 1230. The leached cutter 1220 is similar to the leached cutter 300 (FIG. 3) and has not been treated with any heat treatments, while the second leached cutter 1230 has been affected with a heat treatment. According to the example provided, the heat treatment affecting the second leached cutter 1230 is exposure of the second leached cutter 1230 at 820° C. for five minutes. This heat treatment is an example of the heat exposure that a cutter may be exposed during a brazing process, which is used to couple the cutter onto a downhole tool. Although only on second leached cutter 1230 is shown being exposed to a certain heat treatment, additional second leached cutters 1230 being exposed to a different temperature and/or for a different amount of time can be illustrated in the graphical chart 1200. For example, the temperature exposure can range from 750° C. to 850° C. for a time range from one minute to twenty minutes. However, the exposed temperature may be greater than 850° C. according to certain exemplary embodiments and the time range can be greater or less than the range provided according to certain exemplary embodiments, which may be dependent upon the cutter type used and/or the brazing material used and/or the material used to fabricate the downhole tool. The capacitance axis 1208 includes values for the measured capacitance 1210. A capacitance data point 1240 is obtained by measuring the capacitance of the cutter 1220, 1230, or leached component 1220, 1230, using the capacitance measuring system 400 (FIG. 4), the capacitance measuring system 500 (FIG. 5), capacitance measuring system 1000 (FIG. 10) or a similar type system and is determined according to the description provided with respect to FIG. 13. Each capacitance data point 1240 is plotted on the data scattering chart 1200. Each leached component 1220, 1230 has its capacitance measured a plurality of times. In some exemplary embodiments, five capacitance data points 1240 are obtained for each leached component 1220, 230, however, the number of measurements is greater or fewer in other exemplary embodiments. In some exemplary embodiments, a twenty-five percentile marking 1250, a fifty percentile marking 1252 (or average), and a seventy-five percentile marking 1254 is shown in the chart 1200 for each leached component 1220, 1230. The area between the twenty-five percentile marking 1250 and the seventy-five percentile marking 1254 is shaded. The amount of data scattering is ascertained using this data scattering chart 1200 and can be one or more of a differential between the highest and lowest capacitance measurements 1210 for each leached component 1220, 1230, a range between the twenty-five percentile marking 1250 and the seventy-five percentile marking 1254, or some similar observation made from the data scattering chart 1200.

According to FIG. 12, the leached cutter 1220 is a standard vr46 cutter that has not underwent any heat exposure, while the second leached cutter 1230 also is a standard vr46 cutter, but has underwent heat exposure at 820° C. for five minutes. According to the capacitance measurements, the second leached cutter 1220 has a lower capacitance measurement than the leached cutter 1220. In particular, the second leached cutter 1230 has a capacitance measurement of about 51 pFarads to about 58 pFarads from the twenty-five percentile marking 1250 to the seventy-five percentile marking 1254, respectively. However, the leached cutter 1220 has a capacitance measurement of about 71 pFarads to about 78 pFarads from the twenty-five percentile marking 1250 to the seventy-five percentile marking 1254, respectively. Hence, the graphical chart 1200 shows that the capacitance of a cutter decreases upon being exposed to a heat treatment.

Figure 13:
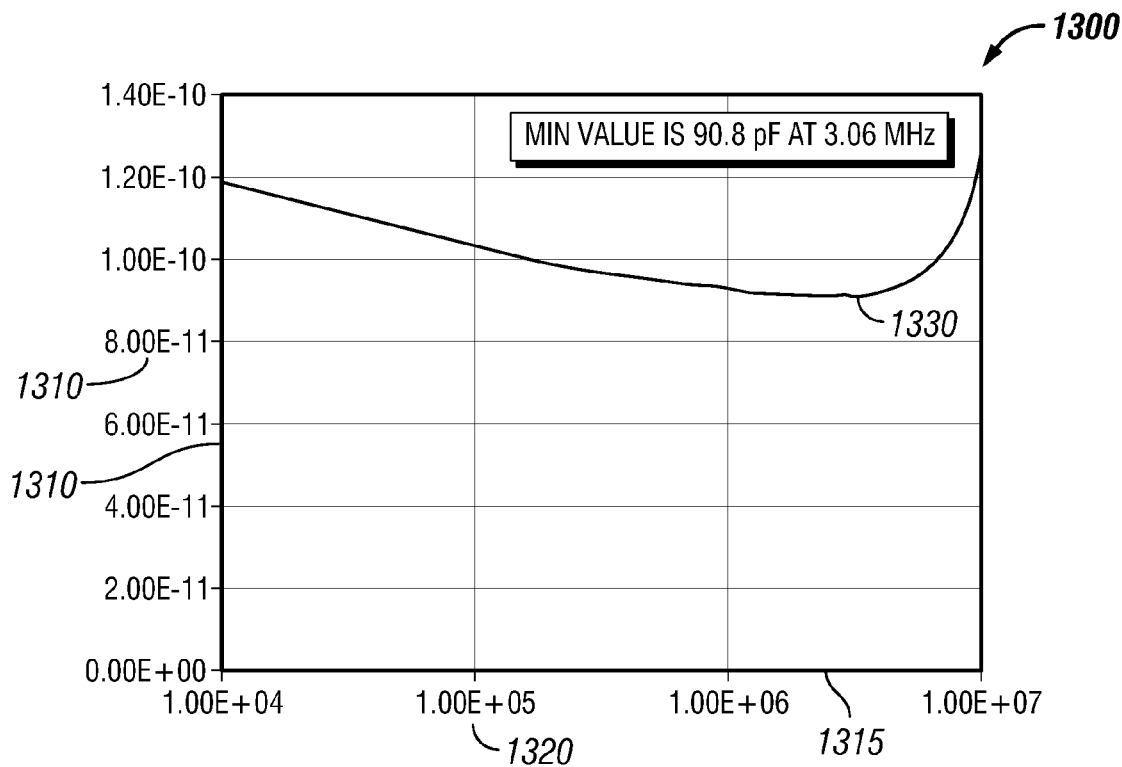
FIG. 13 is a capacitance-to-frequency chart illustrating a relationship between a frequency value and a capacitance value in accordance with an exemplary embodiment of the present invention.

FIG. 13 is a capacitance-to-frequency chart 1300 illustrating a relationship between a capacitance value 1310 and a frequency value 1320 in accordance with an exemplary embodiment of the present invention. Referring to FIG. 13, the capacitance-to-frequency chart 1300 includes a capacitance axis 1308 and a frequency axis 1315. The capacitance 1310 is measured on a leached cutter 300, 1220, 1230 (FIGS. 10 and 12) using impedance spectroscopy in accordance with an exemplary embodiment, which is by frequency sweeping or changing the frequency while measuring capacitance. Accordingly, a capacitance minimum value 1330 is obtained, as shown in the capacitance-to-frequency chart 1300. This capacitance minimum value 1330 is the capacitance value 1210 (FIG. 12) that is used in determining and/or facilitating the determination of the estimated wear resistance of the leached cutter. According to the capacitance-to-frequency chart 1300, the capacitance minimum value 1330 is 90.8 pFarads, which occurs at a frequency value 1320 of 3.06 megahertz; however, these values can differ in other measurements made with different leached cutters.

Although each exemplary embodiment has been described in detail, it is to be construed that any features and modifications that are applicable to one embodiment are also applicable to the other embodiments. Furthermore, although the invention has been described with reference to specific embodiments, these descriptions are not meant to be construed in a limiting sense. Various modifications of the disclosed embodiments, as well as alternative embodiments of the invention will become apparent to persons of ordinary skill in the art upon reference to the description of the exemplary embodiments. It should be appreciated by those of ordinary skill in the art that the conception and the specific embodiments disclosed may be readily utilized as a basis for modifying or designing other structures or methods for carrying out the same purposes of the invention. It should also be realized by those of ordinary skill in the art that such equivalent constructions do not depart from the spirit and scope of the invention as set forth in the appended claims. It is therefore, contemplated that the claims will cover any such modifications or embodiments that fall within the scope of the invention.

What is claimed is:

1. A method of determining wear resistance of a downhole tool, comprising:
   measuring capacitance values of a first plurality of leached polycrystalline diamond compact (PDC) cutters;
   destructively testing wear resistance of each cutter of the first plurality to obtain calibration data;
   brazing a second plurality of leached PDC cutters to the downhole tool, the first plurality and the second plurality being of the same type;
   after brazing, measuring a capacitance value of each cutter of the second plurality; and
   determining an estimated wear resistance of each cutter of the second plurality using the respective measured capacitance value of each cutter of the second plurality and the calibration data,
   wherein:
   multiple capacitance values are measured for each cutter of the second plurality at different frequencies,
   the method further comprises selecting a minimum capacitance value for each cutter of the second plurality, and
   the minimum value is used to determine the estimated wear resistance of each cutter of the second plurality.

2. The method of claim 1, wherein the capacitance value of each cutter of the second plurality is measured by:
   obtaining a capacitance measuring device comprising a positive terminal and a negative terminal;
   electrically coupling a first wire from the positive terminal to a leached layer of the respective cutter; and
   electrically coupling a second wire from the negative terminal to a surface of the downhole tool.

3. The method of claim 2, wherein the first wire is electrically coupled by positioning a first conducting component adjacent to and in contact with the leached layer of the respective cutter and the first wire.

4. The method of claim 3, wherein the first conducting component is cylindrically shaped or annularly shaped.

5. The method of claim 3, wherein the first conducting component is fabricated at least from a copper or copper alloy.

6. The method of claim 3, wherein the first conducting component comprises a conducting material and an insulating material, the insulating material surrounding at least a portion of the perimeter of the conducting material.

7. The method of claim 2, wherein the second wire is electrically coupled by positioning a second conducting component adjacent to and in contact with the surface of the downhole tool and the second wire.

8. The method of claim 7, wherein the second conducting component comprises a foil.

9. The method of claim 7, wherein the second conducting component is fabricated at least from a copper or copper alloy.

10. The method of claim 1, wherein the wear resistance of each cutter of the first plurality is measured using a vertical turret lathe (VTL) test or a granite log test.

11. A method of determining wear resistance of a downhole tool, comprising:
    measuring capacitance values of a first plurality of leached polycrystalline diamond compact (PDC) cutters;
    destructively testing wear resistance of each cutter of the first plurality to obtain calibration data;

brazing a second plurality of leached PDC cutters to the downhole tool, the first plurality and the second plurality being of the same type;

after brazing, measuring a capacitance value of each cutter of the second plurality; and determining an estimated wear resistance of each cutter of the second plurality using the respective measured capacitance value of each cutter of the second plurality and the calibration data, wherein the capacitance value of each cutter of the second plurality is measured by:

obtaining a capacitance measuring device comprising a positive terminal and a negative terminal;

electrically coupling a first wire from the positive terminal to a leached layer of the respective cutter; and electrically coupling a second wire from the negative terminal to a surface of the downhole tool.

12. The method of claim 11, wherein the first wire is electrically coupled by positioning a first conducting component adjacent to and in contact with the leached layer of the respective cutter and the first wire.

13. The method of claim 12, wherein the first conducting component is cylindrically shaped or annularly shaped.

14. The method of claim 12, wherein the first conducting component is fabricated at least from a copper or copper alloy.

15. The method of claim 12, wherein the first conducting component comprises a conducting material and an insulating material, the insulating material surrounding at least a portion of the perimeter of the conducting material.

16. The method of claim 11, wherein the second wire is electrically coupled by positioning a second conducting component adjacent to and in contact with the surface of the downhole tool and the second wire.

17. The method of claim 16, wherein the second conducting component comprises a foil.

18. The method of claim 16, wherein the second conducting component is fabricated at least from a copper or copper alloy.

* * * * *